(12) United States Patent
Rigas et al.

(10) Patent No.: US 8,754,047 B2
(45) Date of Patent: Jun. 17, 2014

(54) PEPTIDE COMPOSITIONS AND METHODS OF USE

(75) Inventors: Basil Rigas, Old Field, NY (US); Yu Sun, Port Jefferson, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 13/015,456

(22) Filed: Jan. 27, 2011

(65) Prior Publication Data

US 2011/0171292 A1  Jul. 14, 2011

Related U.S. Application Data

(63) Continuation-in-part of application No. PCT/US2009/052256, filed on Jul. 30, 2009.

(60) Provisional application No. 61/084,907, filed on Jul. 30, 2008.

(51) Int. Cl.
*A61K 38/00* (2006.01)
*A61K 38/16* (2006.01)
*A61K 38/10* (2006.01)
*A61K 9/127* (2006.01)

(52) U.S. Cl.
USPC ......... 514/19.3; 514/21.3; 514/21.4; 514/6.5; 424/450; 530/324; 530/325; 530/326

(58) Field of Classification Search
None
See application file for complete search history.

(56) References Cited

U.S. PATENT DOCUMENTS

| 5,210,040 | A | 5/1993 | Jou et al. |
| 5,380,531 | A | 1/1995 | Chakrabarti et al. |
| 2002/0103130 | A1 | 8/2002 | Ruoslahti et al. |

FOREIGN PATENT DOCUMENTS

DE  10342784 A1  4/2005

OTHER PUBLICATIONS

Storm et al. 1998. Pharma Sci and Tech Today. 1:19-31.*
Ansell et al. Methods Mol Med 2000:25:51-68.*
Persistent Oxidative Stress in Cancer, Shinya Toyokuni et al. FEBS Letters 358 (1995).
Induction of Oxidative Stress as a Mechanism of Action of Chemopreventive Agents Against Cancer. B. Rigas and Y Sun (British Journal of Cancer (2008) 98, 1157-1160.
Nanoparticle Targeting of Anticancer Drug Improves Therapeutic Response in Animal Model of Human Epithelial Cancer (Cancer Res 2005; 65:12) Jun. 15, 2005.
The Thioredoxin System Mediates Redox-Induced Cell Death in Human Colon Cancer Cells: Implications for the Mechanism of Action of Anticancer Agents (Cancer Res 2008; (20) : 8269-77), Sun et al.
Phosphoasprin (MDC-43), a novel benzyl ester of aspirin, inhibits the growth of human cancer cell lines more potently than aspirin: a redox-dependent effect Rigas et al., Carcinogen.2009 30:512.
Chemopreventive agents induce oxidative stress in cancer cells leading to COX-2 overexpression and COX-2-independent cell death Rigas et al., Carcin2009 30:93.
International Search Report for International Application No. PCT/US2009/052256, filed Jul. 30, 2009.

* cited by examiner

*Primary Examiner* — Shulamith H Shafer
(74) *Attorney, Agent, or Firm* — Kenyon & Kenyon LLP

(57) ABSTRACT

The present invention provides isolated peptides with at least two cysteine residues capable of forming one or more disulfide bonds. Pharmaceutical compositions comprising the isolated peptides of the present invention are also provided. The invention also provides methods for inhibiting, preventing or improving the pathological or clinical manifestations of cancer or an inflammatory disease or disorder in a subject, comprising administering a peptide of the invention.

39 Claims, 13 Drawing Sheets

YJB01

H-ATWCGPCKPRQIKIWFQNRRMKWKK-OH     SEQ ID NO:9

YJB02

H-GTCVNVGCIPRQIKIWFQNRRMKWKK-OH     SEQ ID NO:10

YJB03

H-TCPYCRPRQIKIWFQNRRMKWKK-OH     SEQ ID NO:11

YJB04

H-VCPVCPAPRQIKIWFQNRRMKWKK-OH     SEQ ID NO:12

YJB05

H-ATWAGPAKPRQIKIWFQNRRMKWKK-OH     SEQ ID NO:15

YJB06    H-ATWCGPC-OH    SEQ ID NO:16

YJB07    H-CGHCPRQIKIWFQNRRMKWKK-OH     SEQ ID NO:13

YJB08    H-CPHCPRQIKIWFQNRRMKWKK-OH     SEQ ID NO:14

FIG. 1A

Thioredoxin (Trx):                 -Trp-*Cys*-Gly-Pro-*Cys*-Lys-     (SEQ ID NO:3)

Glutaredoxin (Grx):                -*Cys*-Ser-Tyr-*Cys*-     (SEQ ID NO:4)

Thioredoxin reductase (TrxR):    -*Cys*-Val-Asn-Val-Gly-*Cys*-     (SEQ ID NO:5)

Protein disulfide isomerase (PDI):    -*Cys*-Gly-His-*Cys*-     (SEQ ID NO:6)

Disulfide interchange protein DsbA:    -*Cys*-Pro-His-*Cys*-     (SEQ ID NO:7)

Peroxiredoxin (Prx):             -Val-*Cys*-Pro---(118aa)-Val-*Cys*-Pro-     (SEQ ID NO:8)

FIG. 1B

Gene ID: 7295

PubMed Ref. NM_003329 (SEQ ID NO:1)

TTTGGTGCTTTGGATCCATTTCCATCGGTCCTTACAGCCGCTCGTCAGACTC
CAGCAGCCAAGATGGTGAAGCAGATCGAGAGCAAGACTGCTTTTCAGGAA
GCCTTGGACGCTGCAGGTGATAAACTTGTAGTAGTTGACTTCTCAGCCACG
TGGTGTGGGCCTTGCAAAATGATCAAGCCTTTCTTTCATTCCCTCTCTGAAA
AGTATTCCAACGTGATATTCCTTGAAGTAGATGTGGATGACTGTCAGGATGT
TGCTTCAGAGTGTGAAGTCAAATGCATGCCAACATTCCAGTTTTTTAAGAAG
GGACAAAAGGTGGGTGAATTTTCTGGAGCCAATAAGGAAAAGCTTGAAGCC
ACCATTAATGAATTAGTCTAATCATGTTTTCTGAAAATATAACCAGCCATTGG
CTATTTAAAACTTGTAATTTTTTTAATTTACAAAAATATAAAATATGAAGACAT
AAACCCAGTTGCCATCTGCGTGACAATAAAACATTAATGCT

PubMed Ref. NP_003320 (SEQ ID NO:2)

Met Val Lys Gln Ile Glu Ser Lys Thr Ala Phe Gln Glu Ala Leu Asp Ala Ala
Gly Asp Lys Leu Val Val Val Asp Phe Ser Ala Thr <u>Trp Cys Gly Pro Cys
Lys</u> Met Ile Lys Pro Phe His Ser Leu Ser Glu Lys Tyr Ser Asn Val Ile
Phe Leu Glu Val Asp Val Asp Asp Cys Gln Asp Val Ala Ser Glu Cys Glu
Val Lys Cys Met Pro Thr Phe Gln Phe Phe Lys Lys Gly Gln Lys Val Gly
Glu Phe Ser Gly Ala Asn Lys Glu Lys Leu Glu Ala Thr Ile Asn Glu Leu Val

FIG. 8

SEQUENCE LISTING

<160> NUMBER OF SEQ ID NOS: 16

<210> SEQ ID NO 1
<211> LENGTH: 508
<212> TYPE: DNA
<213> ORGANISM: Homo sapiens

<400> SEQUENCE: 1

```
tttggtgctt tggatccatt tccatcggtc cttacagccg ctcgtcagac tccagcagcc    60
aagatggtga agcagatcga gagcaagact gcttttcagg aagccttgga cgctgcaggt   120
gataaacttg tagtagttga cttctcagcc acgtggtgtg ggccttgcaa aatgatcaag   180
cctttctttc attccctctc tgaaaagtat tccaacgtga tattccttga agtagatgtg   240
gatgactgtc aggatgttgc ttcagagtgt gaagtcaaat gcatgccaac attccagttt   300
tttaagaagg gacaaaaggt gggtgaattt tctggagcca ataaggaaaa gcttgaagcc   360
accattaatg aattagtcta atcatgtttt ctgaaaatat aaccagccat tggctatttta  420 aaacttgtaa ttttttttaat ttacaaaaat ataaaatatg aagacataaa cccagttgcc  480
atctgcgtga caataaaaca ttaatgct                                      508
```

<210> SEQ ID NO 2
<211> LENGTH: 105
<212> TYPE: PRT
<213> ORGANISM: Homo sapiens

<400> SEQUENCE: 2

```
Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105
```

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

```
Trp Cys Gly Pro Cys Lys
1               5
```

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

```
<400> SEQUENCE: 4

Cys Ser Tyr Cys
1

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5

Cys Val Asn Val Gly Cys
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Cys Gly His Cys
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Cys Pro His Cys
1

<210> SEQ ID NO 8
<211> LENGTH: 124
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(121)
<223> OTHER INFORMATION: Xaa can be any amino acid

<400> SEQUENCE: 8

Val Cys Pro Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Val Cys Pro
```

```
                115                 120

<210> SEQ ID NO 9
<211> LENGTH: 25
<212> TYPE: PRT
<213> ORGANISM: Artificial sequence
<220> FEATURE:
<223> OTHER INFORMATION: Synthetic peptide

<400> SEQUENCE: 9

Ala Thr Trp Cys Gly Pro Cys Lys Pro Arg Gln Ile Lys Ile Trp Phe
1               5                   10                  15

Gln Asn Arg Arg Met Lys Trp Lys Lys
            20                  25

<210> SEQ ID NO 10
<211> LENGTH: 26
<212> TYPE: PRT
<213> ORGANISM: Artificial sequence
<220> FEATURE:
<223> OTHER INFORMATION: Synthetic peptide

<400> SEQUENCE: 10

Gly Thr Cys Val Asn Val Gly Cys Ile Pro Arg Gln Ile Lys Ile Trp
1               5                   10                  15

Phe Gln Asn Arg Arg Met Lys Trp Lys Lys
            20                  25

<210> SEQ ID NO 11
<211> LENGTH: 23
<212> TYPE: PRT
<213> ORGANISM: Artificial sequence
<220> FEATURE:
<223> OTHER INFORMATION: Synthetic peptide

<400> SEQUENCE: 11

Thr Cys Pro Tyr Cys Arg Pro Arg Gln Ile Lys Ile Trp Phe Gln Asn
1               5                   10                  15

Arg Arg Met Lys Trp Lys Lys
            20

<210> SEQ ID NO 12
<211> LENGTH: 24
<212> TYPE: PRT
<213> ORGANISM: Artificial sequence
<220> FEATURE:
<223> OTHER INFORMATION: Synthetic peptide

<400> SEQUENCE: 12

Val Cys Pro Val Cys Pro Ala Pro Arg Gln Ile Lys Ile Trp Phe Gln
1               5                   10                  15

Asn Arg Arg Met Lys Trp Lys Lys
            20

<210> SEQ ID NO 13
<211> LENGTH: 21
<212> TYPE: PRT
<213> ORGANISM: Artificial sequence
<220> FEATURE:
<223> OTHER INFORMATION: Synthetic peptide

<400> SEQUENCE: 13

Cys Gly His Cys Pro Arg Gln Ile Lys Ile Trp Phe Gln Asn Arg Arg
1               5                   10                  15

Met Lys Trp Lys Lys
```

```
               20

<210> SEQ ID NO 14
<211> LENGTH: 21
<212> TYPE: PRT
<213> ORGANISM: Artificial sequence
<220> FEATURE:
<223> OTHER INFORMATION: Synthetic peptide

<400> SEQUENCE: 14

Cys Pro His Cys Pro Arg Gln Ile Lys Ile Trp Phe Gln Asn Arg Arg
1               5                   10                  15

Met Lys Trp Lys Lys
            20

<210> SEQ ID NO 15
<211> LENGTH: 25
<212> TYPE: PRT
<213> ORGANISM: Artificial sequence
<220> FEATURE:
<223> OTHER INFORMATION: Synthetic peptide

<400> SEQUENCE: 15

Ala Thr Trp Ala Gly Pro Ala Lys Pro Arg Gln Ile Lys Ile Trp Phe
1               5                   10                  15

Gln Asn Arg Arg Met Lys Trp Lys Lys
            20                  25

<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Ala Thr Trp Cys Gly Pro Cys
1               5
```

PEPTIDE COMPOSITIONS AND METHODS OF USE

CROSS-REFERENCE TO RELATED APPLICATIONS

The present application is a continuation-in-part application of International Application Serial No. PCT/US2009/052256, filed on Jul. 30, 2009, which claims the benefit of U.S. Provisional Application No. 61/084,907, filed Jul. 30, 2008, which is hereby incorporated by reference in its entirety.

SEQUENCE LISTING

The specification further incorporates by reference the Sequence Listing submitted herewith via EFS on Jan. 27, 2011. Pursuant to 37 C.F.R. §1.52(e)(5), the Sequence Listing text file, identified as 0726000297.txt, is 6.32 kilobytes and was created on Jan. 27, 2011. The Sequence Listing, electronically filed herewith, does not extend beyond the scope of the specification and thus does not contain new matter.

BACKGROUND OF THE INVENTION

Redox biochemistry is fundamental to life. The energy needs of complex organisms require vast amounts of ATP. The supply of ATP depends heavily on redox chemistry, as it is driven by changes in free energy associated with electron or hydrogen transfers (Frein et al., (2005) *Biochem Pharmacol* 70:811-823). Technically, redox, shorthand for reduction/oxidation, describes all chemical reactions in which the oxidation state of atoms changes. In simpler terms, oxidation describes the loss of electrons by a molecule, atom, or ion and reduction describes the gain of electrons by the same.

Redox signaling is the concept that electron-transfer processes play a key messenger role in biological systems. At the heart of redox signaling are the so-called reactive oxygen species (ROS), including oxygen radicals (e.g., $O_2.^-$ and $OH.$) and also nonradical derivatives of $O_2$ ($H_2O_2$). The discovery of reactive nitrogen species expanded this term to "reactive oxygen and nitrogen species" (RONS). Free radicals contain one or more unpaired electrons. Since molecules seek to be balanced, that is to have an equal number of protons and electrons, the unpaired electron spins of these radicals make them highly reactive.

RONS are produced continuously by the mitochondria ($O_2.^-$, $OH.$ and $H_2O_2$,) of most cells and also by cytochrome P450 ($O_2.^-$, and $H_2O_2$), macrophages, ($O_2^{-.}$, $^H{}_2O_2$, and NO) and peroxisomes ($H_2O_2$) (Klaunig, et al., (2004) *Annu Rev Pharmacol Toxicol* 44:239-267; Genestra, M., (2007) *Cell Signal* 19:1807-1819). During mitochondrial oxidative metabolism, about 5% of oxygen is converted primarily into $O_2$, whereas 95% of it is reduced to water. Given the high reactivity of RONS, it is not surprising that the cell has invested heavily into an antioxidant defense system to contain RONS. This defense system includes: (a) classic antioxidant enzymes, such as superoxide dismutase (SOD), catalase, glutathione (GSH) peroxidase, glutaredoxin, and thioredoxin, which are distributed in mitochondria, peroxisomes, and cytoplasm; (b) Nonclassic antioxidant enzymes, for example, heme oxygenase-1; (c) Phase II detoxifying enzymes, recently shown to be protective, such as GSH reductase, NQO1, and GSH transferase1; and (d) nonenzymatic antioxidants, such as vitamins E and C, GSH, and catechins.

For many years, it has been widely assumed that all RONS are bad for the cell. Consequently, research efforts have been generally focused on suppressing RONS, hoping to prevent or even reverse RONS-related biological damage. Reactive oxygen and nitrogen species, however, have what can be termed 'multiple biological personalities:' at low concentrations they protect the cell; at higher concentrations they can damage many biological molecules, such as DNA, proteins, and lipids; and yet, they can also help prevent cancer by initiating the death of the transformed cell.

Recently an important conceptual distinction has become clear with regard to the roles reactive oxygen and nitrogen species play in cellular physiology. (Frein et al., (2005) *Biochem Pharmacol* 70:811-823); Halliwell, B., (2007) *Biochem J* 401:1-11). First, it has been well-established that there exists a network of redox-based regulatory mechanisms that are often quite relevant to carcinogenesis, but which are not necessarily pathophysiological. Second, it is also clear that disturbed redox equilibrium is indeed pathophysiological and such disturbances have been described for years as 'oxidative stress.' These findings have led to the delineation between redox signaling and oxidative stress. Redox signaling embraces a reversible phase of physiological regulatory reactions occurring over short time periods where the signal is passed via the addition and loss of electrons. These regulatory reactions relate primarily the main cellular redox systems, e.g., GSH, ascorbate, vitamin E, lipoic acid, NADPH, or NADH. In this type of signaling, the oxidative reactions, which often lead to posttranslational protein modification, are returned to the resting state by reductive pathways. Such posttranslational modifications include glutathiolation, S-nitrosylation, methionine sulphoxidation, and oxidations with disulfide formation. In contrast, oxidative stress denotes a persistent and often irreversible oxidative shift that characterizes a pathophysiological state. Oxidative stress has been defined as an imbalance between oxidants and antioxidants in favor of the former, resulting in increased cellular levels of RONS. Oxidative stress is implicated in the pathogenesis of several diseases including cancer, inflammatory disorders, cardiovascular and neurodegenerative disorders, sepsis, reperfusion damage, rheumatoid arthritis, osteoarthritis, and diabetes.

There is significant evidence for a role of RONS in cancer. Specific activities where RONS have been implicated include genotoxicity, promotion of transformed cell growth and angiogenesis, as well as the regulation of apoptosis. For example, persistent oxidative stress has been suggested in Toyokuni et al., (1995) to contribute to oncogene activation, genomic instability, chemotherapy resistance, and even invasion and metastasis. (Toyokuni et al., (1995) *FEBS Lett* 358: 1-3). Nuclear factor-kB (NF-kB), MAPK cascades as well as GSH and related antioxidant pathways are suggested to be the mediators of such RONS-related activity. Chronic inflammation, which is widely considered to be connected to carcinogenesis, is another source of RONS. The linkage of RONS generated by inflammation to cancer has also been postulated. Similarly, the hypoxiainducible factor-1a (HIF-1a) is linked to cancer through its regulation by RONS. (Pouyssegur et al., (2006) *Biol Chem* 387:1337-1346). In particular, RONS signaling can account for the high levels of HIF-1a in normoxic areas of tumors. Hypoxia-inducible factor promotes survival in low oxygen conditions, like those encountered in many cancerous tumors, by upregulating an array of hypoxia-induced genes, including the vascular endothelial factor, which promotes angiogenesis. Finally, RONS have been associated with the induction of apoptotic and necrotic cell death, the specific outcome depending on, inter alia, the cellular levels of RONS.

As noted in Rigas, B., and Sun, Y., (2008), altering the redox status of a cancer cell can result in the death of that cell. (Rigas, B., and Sun, Y., (2008) *British J. of Cancer*, 98:1157-1160, the contents of which are expressly incorporated by reference herein). In particular, Rigas and Sun were able to establish that increased production of RONS leads to oxidative stress and apoptosis in cancer cells. Thus, intervention in the redox state of a particular cancer cell provides a strategy for treatment and/or prevention of that cancer. In fact, various anticancer agents are already well-known to induce the production of RONS and induce cell death through oxidative stress, including the topoisomerase inhibitor etoposide (Oh et al., (2007) *Mol Cancer Ther* 6:2178-2187), arsenic trioxide (Nakagawa et al., (2002) *Life Sci* 70:2253-2269), and cisplatin (Berndtsson et al., (2007) *Int J Cancer* 120:175-180).

For a long time, reactive oxygen species have been considered harmful mediators of inflammation owing to their highly reactive nature. However, emerging findings suggest that ROS can be anti-inflammatory and prevent autoimmune responses, thus challenging existing dogma. For instance, ROS produced by the phagocyte NADPH oxidase (NOX2) complex might be produced as a mechanism to fine-tune the inflammatory response. (Hultqvist et al., (2009) *Trends Immunol.* 30(5):201-208). To illustrate this point further, recent evidence suggests that NO and its redox derivatives may protect joints affected by osteoarthritis, a degenerative disease involving chondrocytes and cartilage (Abramson, (2008) *Arthritis Res Ther.* 10 Suppl 2:52). NO and its derivatives have a similarly protective involvement in nociception and pain, which may contribute to the functional disability of osteoarthritis. A similar understanding has been developed for other inflammation-related clinical entities. The critical role of inappropriate inflammation is becoming accepted in many diseases, including cardiovascular diseases, inflammatory and autoimmune disorders, neurodegenerative conditions, infection and cancer (Smith, G. and Missailidis, S., (2004) *Journal of Inflammation* 1:3 and Zhang, Z. and Rigas, B., (2006) *Int J Oncol.* 29(1):185-92).

There is a continuing need in the art to identify new therapies for RONS-related pathologies, e.g., cancer, inflammatory disorders, cardiovascular disorders, neurodegenerative disorders, sepsis, reperfusion damage, rheumatoid arthritis, osteoarthritis, and diabetes, including a need for new agents that function via the inducing the production of RONS. The present invention provides an entirely new class of such RONS-generating agents.

SUMMARY OF THE INVENTION

In one aspect, the present invention provides isolated peptides with at least two cysteine residues capable of forming one or more disulfide bonds. Such peptides can include additional functional sequences, including, by way of example and not by way of limitation, targeting sequences (e.g., antibody sequences and antibody mimetic sequences) and cell penetrating sequences (e.g., penetratin, Tat, and protegrin 1 (PG-1) antimicrobial peptide SynB), and/or be covalently or non-covalently bound to secondary compounds (e.g., chemotherapeutics, vaccines, and immunogenic compositions).

In one embodiment, the peptides of the instant invention comprise the sequence:

$$Y_1\text{-}(x)n\text{-}Cys\text{-}(y)N\text{-}Cys\text{-}(z)n\text{-}Y_2$$

where:
x, y, and z=any amino acid;
n=any number;
N=any number that allows formation of one or more intramolecular disulfide bonds;
$Y_1$ is hydrogen or an amino-derivative group and $Y_2$ is hydrogen or a carboxy-derivative group;
wherein an intramolecular disulfide bond is formed between the two cysteine residues.

In certain embodiments, the peptide includes additional cysteine residues and intramolecular disulfide bonds.

In certain embodiments, (y)N is selected from the group consisting of Gly-Pro, Ser-Tyr, Val-Asn-Val-Gly, Gly-His, Pro-His, and Pro-118 amino acids-Val.

In certain embodiments, the invention provides an isolated peptide comprising the amino acid sequence corresponding to the sequence of the active site of: thioredoxin, SEQ ID NO:3; glutaredoxin, SEQ ID NO:4; thioredoxin reductase, SEQ ID NO:5; protein disulfide isomerase, SEQ ID NO:6; disulfide interchange protein DsbA, SEQ ID NO:7; peroxiredoxin, SEQ ID NO:8; or a fragment, analog, derivative, or peptidomimetic thereof.

In certain embodiments, the invention provides an isolated peptide comprising the amino acid sequence of: YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof. In another embodiment, the invention provides an isolated peptide consisting of the amino acid sequence of YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof.

In other embodiments, the isolated peptide includes an amino acid sequence that is at least about 70% homologous to the amino acid sequence of YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14 and retains the sequence Cys-(y)N-Cys, where y is any amino acid and N is any number, and contains one or more disulfide bridge. In another embodiment, the isolated peptide includes an amino acid sequence that is about 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99% homologous to the amino acid sequence of YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14, and retains the sequence Cys-(y)N-Cys, where y is any amino acid and N is any number, and contains one or more disulfide bridge.

In another embodiment, the invention provides pharmaceutical compositions comprising a peptide of the invention in combination with a pharmaceutically acceptable carrier. In certain embodiments the invention provides pharmaceutical compositions wherein the peptide of the invention is present in a composition comprising a covalently or non-covalently attached carrier protein, such as a cell penetrating protein. In certain embodiments the invention provides pharmaceutical compositions wherein the peptide of the invention is incorporated in a liposome. In certain embodiments the invention provides pharmaceutical compositions wherein the peptide of the invention is covalently or non-covalently attached to a nanoparticle, such as a dendrimer.

In another embodiment of the invention, nucleic acid molecules encoding the peptides of the invention, portions thereof, as well as recombinant expression vectors that include the nucleic acids of the invention, and host cells transfected with such vectors, are provided.

In another aspect, the invention provides methods for administering a peptide of the invention to a subject to inhibit, prevent, or improve the pathological or clinical manifestations of cancer, inflammatory disorders, cardiovascular disorders, neurodegenerative disorders, sepsis, reperfusion damage, rheumatoid arthritis, osteoarthritis, or diabetes. Such methods include inhibiting the growth of tumors as well as the induction of tumor regression.

In certain embodiments of the invention, a method of inhibiting cancer in a subject is provided. In certain embodiments of the invention, the method of inhibiting cancer in a subject comprises administration of a therapeutically effective amount of a peptide comprising an amino acid sequence comprising at least two cysteine residues capable of forming one more disulfide bridges and having the general formula: (x)n-Cys-(y)N-Cys-(z)n, where x, y, and z=any amino acid, n=any number, and N=any number which allows for the formation of one or more disulfide bridges, to thereby inhibit cancer in the subject. In certain embodiments, (y)N is selected from the group consisting of Gly-Pro, Ser-Tyr, Val-Asn-Val-Gly, Gly-His, Pro-His, and Pro-(0 to 118 amino acids)-Val. In certain embodiments, the administered peptide comprises an amino acid sequence corresponding to the sequence of the active site of: thioredoxin, SEQ ID NO:3; glutaredoxin, SEQ ID NO:4; thioredoxin reductase, SEQ ID NO:5; protein disulfide isomerase, SEQ ID NO:6; disulfide interchange protein DsbA, SEQ ID NO:7; peroxiredoxin, SEQ ID NO:8; or a fragment, analog, derivative, or peptidomimetic thereof. In certain embodiments, the administered peptide comprises the amino acid sequence of: YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof. In certain embodiments, the administered peptide consists of the amino acid sequence of YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof.

In certain embodiments, the cancer being inhibited selected from the group consisting of colon cancer, pancreatic cancer, and breast cancer.

In certain embodiments, the method of inhibiting cancer further comprises administering to the subject one or more additional anti-cancer agents. In certain embodiments, the additional anti cancer agent(s) is a chemotherapeutic agent. In certain embodiments, the subject is human.

In certain embodiments of the invention, a method inhibiting, an inflammatory disease, a neurodegenerative disease, a cardiovascular disease, or a rheumatological disease or disorder in the subject is provided. In certain embodiments, the method of inhibiting an inflammatory disease, a neurodegenerative disease, a cardiovascular disease, or a rheumatological disease or disorder, comprises administration of a therapeutically effective amount of a peptide comprising an amino acid sequence comprising at least two cysteine residues capable of forming one or more disulfide bridges and having the general formula: (x)n-Cys-(y)N-Cys-(z)n (where x, y, and z=any amino acid, n=any number, and N=any number which allows for the formation of one or more disulfide bridges), to a subject. In certain embodiments, (y)N is selected from the group consisting of Gly-Pro, Ser-Tyr, Val-Asn-Val-Gly, Gly-His, Pro-His, and Pro-118 amino acids-Val. In certain embodiments, the administered peptide comprises an amino acid sequence corresponding to the sequence of the active site of: thioredoxin, SEQ ID NO:3; glutaredoxin, SEQ ID NO:4; thioredoxin reductase, SEQ ID NO:5; protein disulfide isomerase, SEQ ID NO:6; disulfide interchange protein DsbA, SEQ ID NO:7; peroxiredoxin, SEQ ID NO:8; or a fragment, analog, derivative, or peptidomimetic thereof. In certain embodiments, the administered peptide comprises the amino acid sequence of: YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof. In certain embodiments, the administered peptide consists of the amino acid sequence of YJB01, SEQ ID NO:9; YJB02, SEQ ID NO:10; YJB03, SEQ ID NO:11; YJB04, SEQ ID NO:12, YJB07, SEQ ID NO:13; YJB08, SEQ ID NO:14; or a fragment, analog, derivative, or peptidomimetic thereof.

In certain embodiments, the neurodegenerative disease is Alzheimer's disease. In certain embodiments, the cardiovascular disease is coronary artery disease. In additional embodiments, the rheumatological disease is rheumatoid arthritis, osteoarthritis, or lupus.

Other features and advantages of the instant invention will be apparent from the following detailed description and examples, which should not be construed as limiting.

BRIEF DESCRIPTION OF THE DRAWINGS

FIGS. 1A-B illustrate synthesized peptides based on the structure of the active sites of thioredoxin, thioredoxin reductase, glutaredoxin, peroxiredoxin, protein disulfide isomerase, and disulfide interchange protein DsbA (FIG. 1A) as well as the sequences of the active sites of thioredoxin, glutaredoxin, and thioredoxin reductase, protein disulfide isomerase, disulfide interchange protein DsbA, and peroxiredoxin (FIG. 1B).

FIG. 1A illustrates the synthesized peptide "YJB01" (SEQ ID NO:3). The YJB01 peptide contains eight amino acids of thioredoxin (underlined) which represent amino acid residues A29 to K36, including C32 and C35 (bolded), of the human thioredoxin protein (full length sequence provided as SEQ ID NO:2, active site sequence provided as SEQ ID NO:3). YJB01 also contains 16 additional amino acids (residues P9 through K25 of SEQ ID NO:9) which facilitate its access into the cell. FIG. 1A also shows YJB02 (SEQ ID NO:10), which contains the six amino acids of the thioredoxin reductase active site and the same 16 amino acids as YJB01 to facilitate access into the cell; YJB03 (SEQ ID NO:11), which is based on the four amino acid active site sequence of glutaredoxin; YJB04 (SEQ ID NO:12), which is based on a truncated version of the active site of peroxiredoxin; YJB07 (SEQ ID NO:13), which contains the four amino acid active site sequence of protein disulfide isomerase; and YJB08 (SEQ ID NO:14), which contains the four amino acid active site sequence of disulfide interchange protein DsbA. FIG. 1A also shows YJB05 (SEQ ID NO:15), a control peptide where the two bolded cysteines from YJB01 have been replaced by two alanines, and YJB06 (SEQ ID NO:16) a control peptide where amino acids K8-K25 of YJB01, including the sequence employed to facilitate access into the cell have been deleted.

FIG. 1B shows the active sites for thioredoxin (Trx) (SEQ ID NO:3), glutaredoxin (Grx) (SEQ ID NO:4), thioredoxin reductase (TrxR) (SEQ ID NO:5), protein disulfide isomerase (PDI) (SEQ ID NO:6), disulfide interchange protein DsbA (SEQ ID NO:7), and peroxiredoxin (SEQ ID NO:8).

FIGS. 2A1-A8 show in vitro MTT (3-(4,5-Dimethyl-2-thiazolyl)-2,5-diphenyl-2H-tetrazolium bromide) staining of cultured human colon (HT29) cancer cells as photographed with a phase-contrast microscope. FIGS. 2A1 and 2A5 show cells treated with DMSO control. FIG. 2A2 shows cells treated with DTT 1 mM. FIG. 2A3 shows cells treated with the YJB01 peptide 50 μM after the YJB01 peptide was pretreated with 1 mM DTT to reduce its disulfide bond. FIG. 2A4 shows cells treated with 100 μM after the YJB01 peptide was pretreated with 1 mM DTT to reduce its disulfide bond. FIG. 2A6 shows cells treated with 25 μM YJB01. FIG. 2A7 shows cells treated with 50 μM YJB01. FIG. 2A8 shows cells treated with 100 μM YJB01.

FIGS. 2B1-B6 show in vitro MTT (3-(4,5-Dimethyl-2-thiazolyl)-2,5-diphenyl-2H-tetrazolium bromide) staining of cultured human colon (SW480) cancer cells as photographed with a phase-contrast microscope. FIG. 2B1 shows cells treated with DMSO control. FIG. 2B2 shows cells treated with DTT 1 mM. FIG. 2B3 shows cells treated with 50 μM YJB01 after the YJB01 peptide was pretreated with 1 mM DTT to reduce its disulfide bond. FIG. 2B4 shows cells treated with 100 μYJB01 after the YJB01 peptide was pretreated with 1 mM DTT to reduce its disulfide bond. FIG. 2B5 shows cells treated with 50 μM YJB01. FIG. 2B6 shows cells treated with 100 μM YJB01.

Immunodeficient SCID mice (from Jackson Lab) were transplanted subcutaneously to their flank with 1.5 million SW480 human colon cancer cells. After the tumor size reached 120-150 mm$^3$, one mouse was treated with 100 μg YJB01 peptide injected intraperitoneally once a day, and the other one was treated with DMSO as a vehicle control. The tumor size was measured every two days (see FIG. 3A and FIG. 3B). The tumor volume was calculated based on its length (L) and width (W) using the formula Tumor volume=LW(L+W/2)0.56. (Rigas, B., and Kozoni, V., (2008) International Journal of Oncology, 32: 97-100). On the 10th day of treatment, the tumor volume was determined, the SCID mice were sacrificed and the tumors were excised and their weight was recorded (FIG. 3B).

Figure 2A:
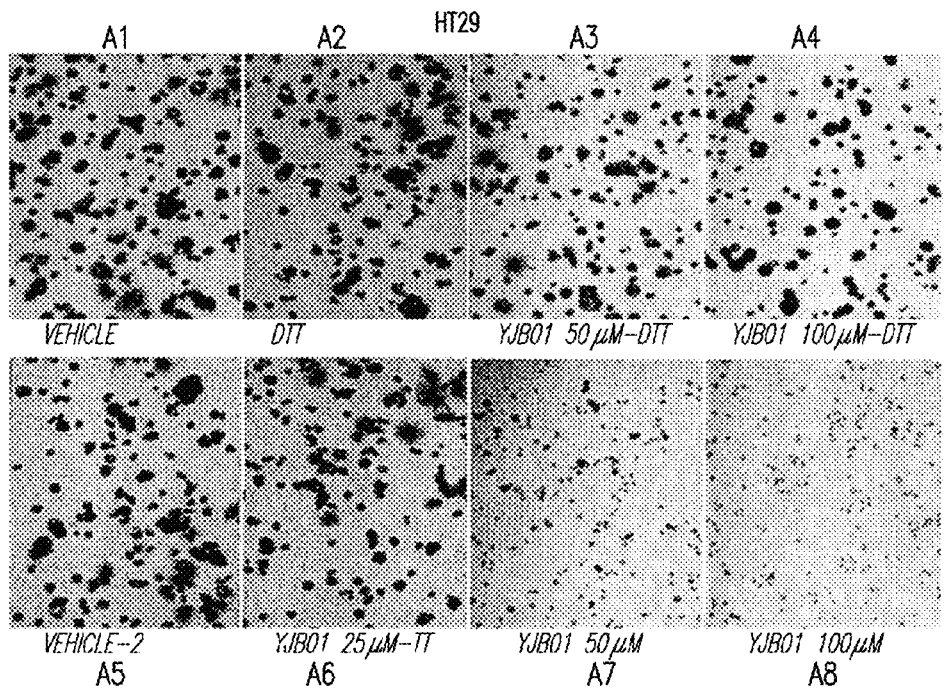
Figure 2B:
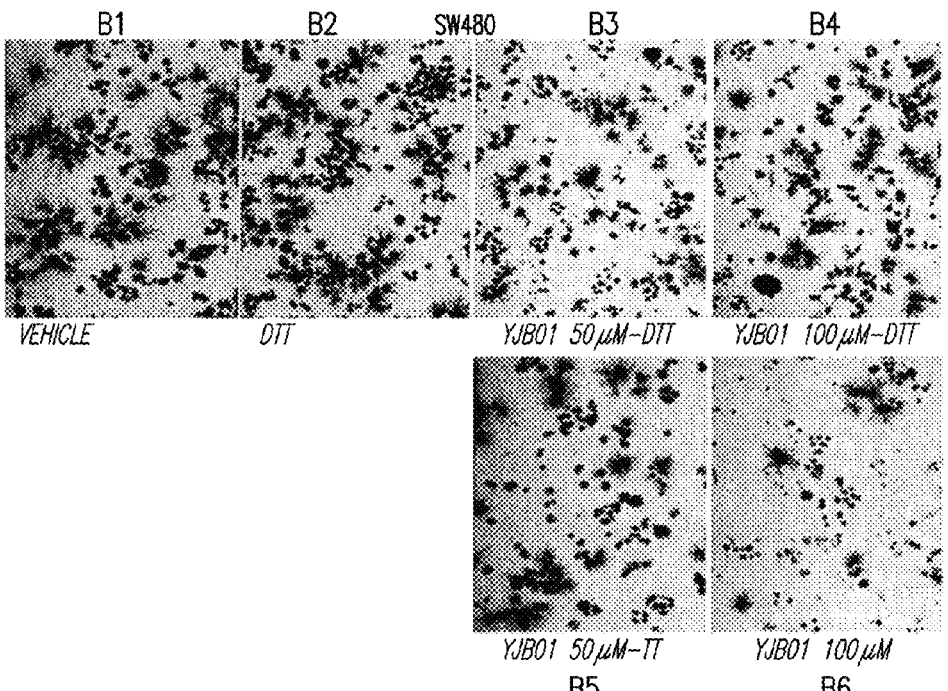
Figure 3A:
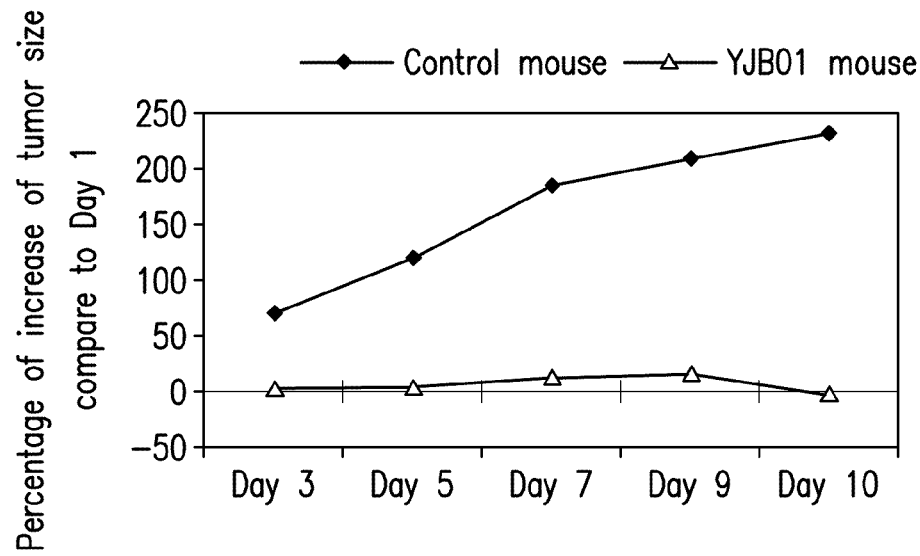
FIGS. 3A-B are graphs illustrating the results of studies of SW480 human colon cancer cell xenografts in immunodeficient SCID mice treated with peptides of the invention.
Figure 3B:
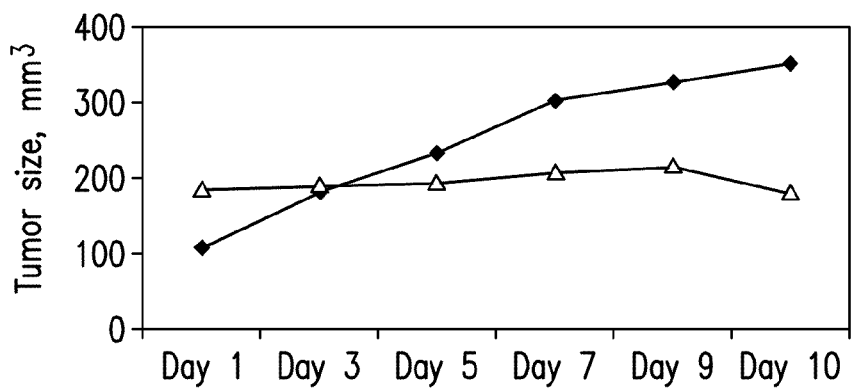

After 10 days of treatment with the YJB01 peptide, there was almost no growth (−4% at day 10 comparing with day 1, as shown by the red line in FIG. 3A) of the tumor, whereas in the control animal (treated with vehicle only) the tumor size increased by 229%, as shown by the blue line in FIG. 3B.

Figure 4A:
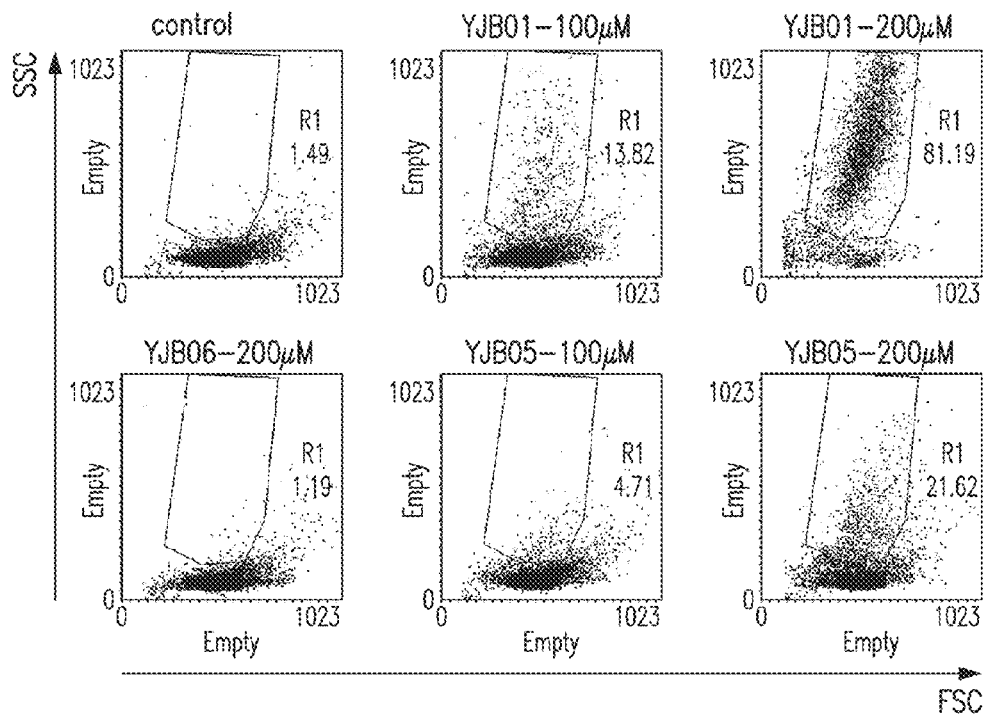
Figure 4B:
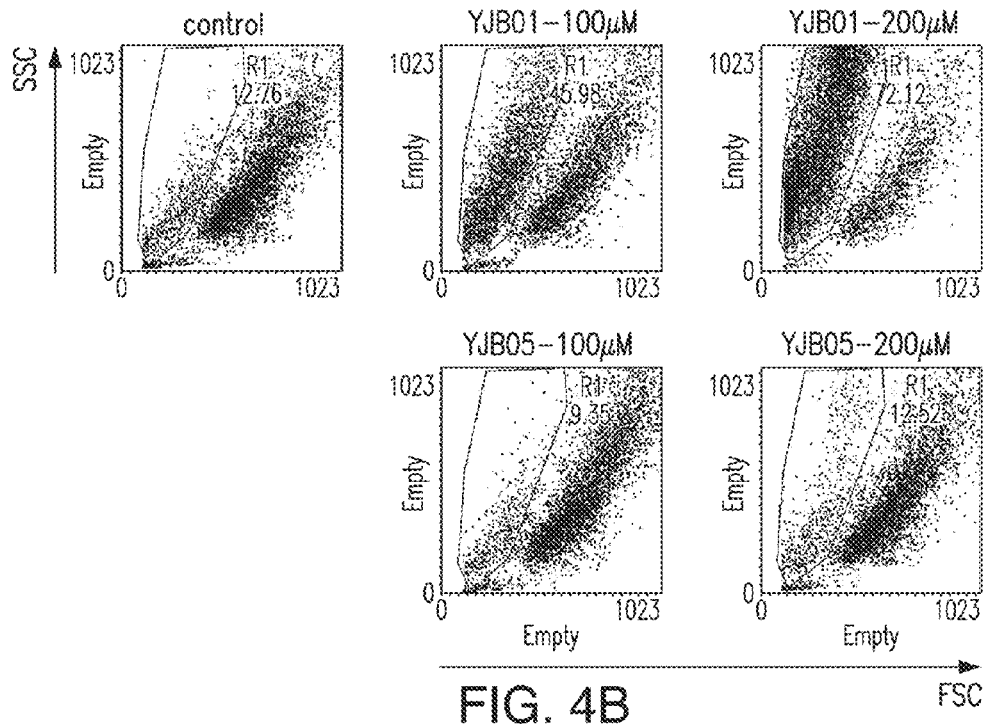

FIGS. 4A-B are histograms plotting the side scatter (SSC) (cell density) and forward scatter (FSC) (cell size) of flow cytometric analyses involving the administration of YJB01, YJB05, or YJB06 to SW480 human colon cancer cells and MCF-7 human breast cancer cells to identify the cytokinetic effect of YJB01, YJB05 or YJB06 peptides on SW480 and MCF-7 cells.

SW480 human colon cancer cells and MCF7 breast cancer cells were grown following the instructions of American Type Culture Collection (ATCC, Monassas, Va.). The cells were treated with the test peptides (YJB01, YJB05, or YJB06) for 24 hrs at concentrations ranging from 0 μM, to 200 μM and subjected to flow cytometric analysis following standard protocols.

Compared with YJB05 and YJB06, YJB01 had a greater cell killing effect in both cancer cell lines (studies involving SW480 cells are show in FIG. 4A, studies involving MCF7 cells are shown in FIG. 4B). Following treatment for 24 hr with 200 μM YJB01, 81.19% of SW480 and 72.12% of MCF7 cells were dead. However, following treatment for 24 hr with 200 μM YJB05 there were only 21.62% and 12.52% dead cells in SW480 and MCF7 cells, respectively. These findings indicate that the disulfide bond between the two cysteine residues is critical to the cell killing effect of these peptides. The cell killing effect of YJB06, which lacks the cell membrane permeable tail, was also tested in SW480 cells. As shown in FIG. 4A, YJB06 failed to kill SW480 colon cancer cells.

Figure 5A:
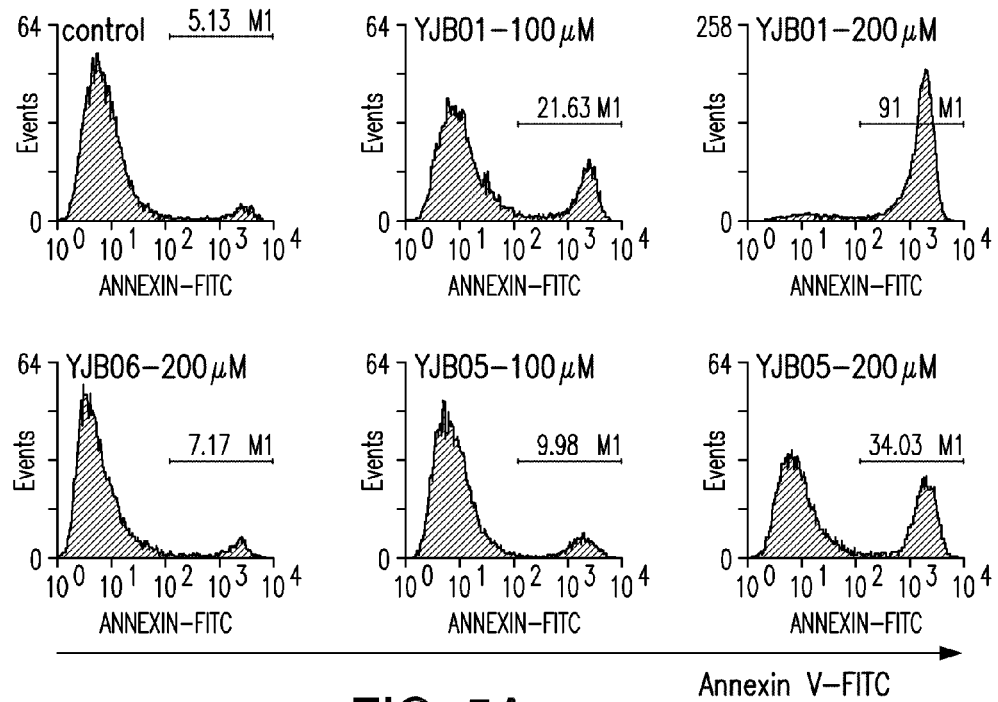
Figure 5B:
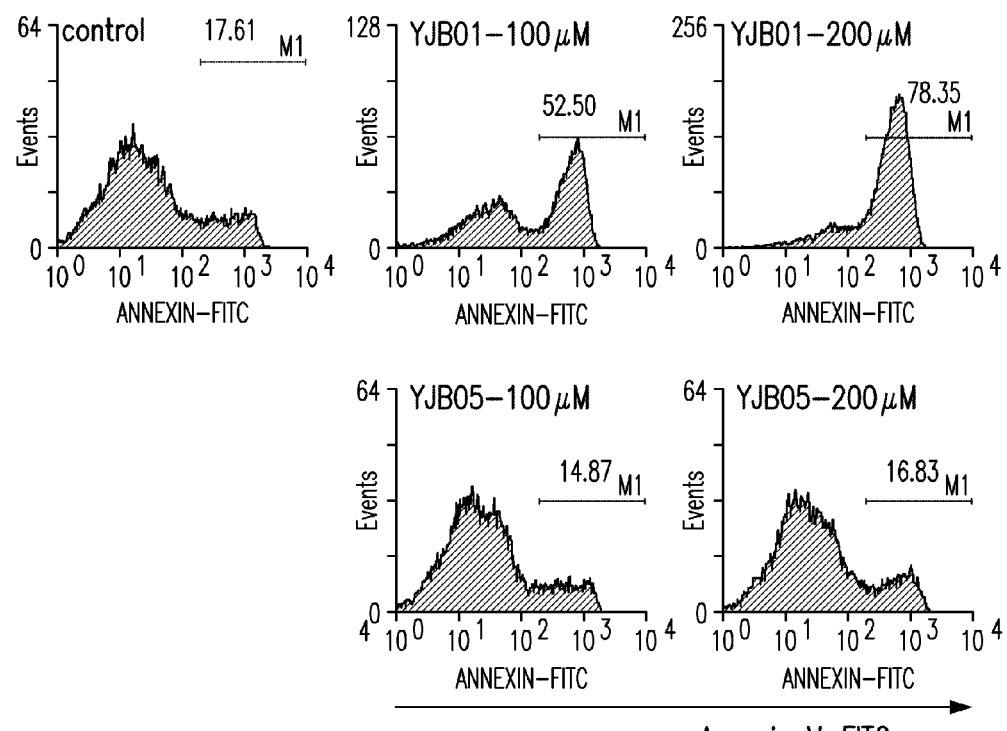

FIGS. 5A-B are histograms of flow cytometric analyses comparing the apoptotic effect of YJB01, YJB05 and YJB06 peptides on SW480 human colon cancer cells (FIG. 5A) and MCF-7 human breast cancer cells (FIG. 5B).

SW480 human colon cancer cells and MCF7 breast cancer cells were grown following the instructions of American Type Culture Collection (ATCC, Monassas, Va.). The cells were treated with the test peptides (YJB01, YJB05, or YJB06) for 24 hrs at concentrations ranging from 0 μM, to 200 μM. After treatment, cells were trypsinized and stained with Annexin V-FITC (100× dilution) for 15 minutes. Annexin V-FITC fluorescence intensities were analyzed by FACSCaliber (BD Bioscience) following standard protocols. Annexin V (+) cells are apoptotic cells. Thus, FIG. 5A-B demonstrates the cell killing effect of the YJB01 peptide in SW480 and MCF7 cancer cells, confirming by an independent method the results shown in FIG. 4.

Figure 6A:
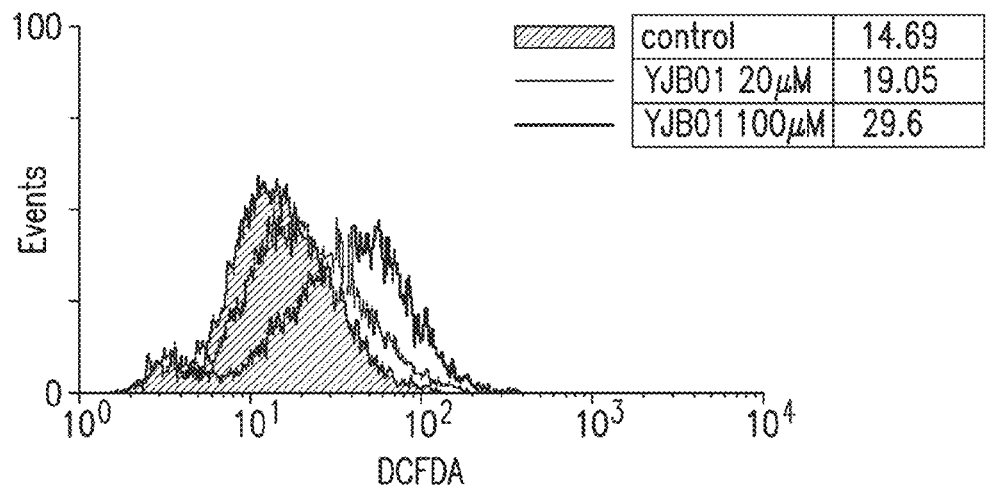
Figure 6B:
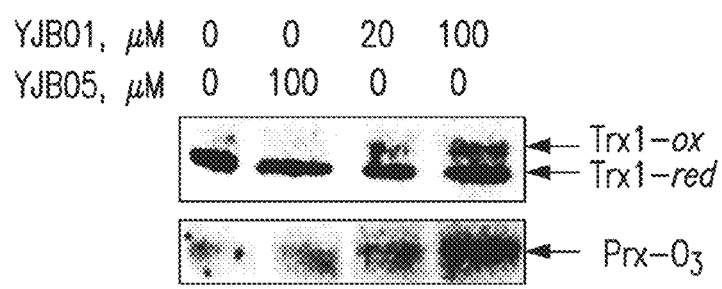

FIGS. 6A-B illustrate the ability of YJB01 to induce RONS production in SW480 human colon cancer cells and its ability to oxidize thioredoxin 1 and peroxiredoxin 1.

FIG. 6A shows the levels of RONS in SW480 cells treated with YJB01 at 20 μM and 100 μM (and negative control) via the detection of the general RONS probe, dichlorodihydrofluorescein diacetate (DCFDA). SW480 human colon cancer cells were grown following the instructions of American Type Culture Collection (ATCC, Monassas, Va.). The cells were treated with the test peptide YJB01 for 1 hr at either 20 μM or 100 μM. After treatment, cells were trypsinized and stained with DCFDA (10 μmol/L) for 30 minutes at 37° C. DCFDA fluorescence intensity was analyzed by FACSCaliber (BD Bioscience) following standard protocols. As illustrated in FIG. 5A, the Geometric Mean of the fluorescence intensity of DCFDA was increased significantly from 14.69 to 19.05 and then to 29.6 in SW480 cells after treatment with YJB01 (at concentrations of 20 μM and 100 μM, respectively). Thus, FIG. 6A indicates YJB01 induces RONS production in a concentration dependent manner.

FIG. 6B illustrates that YJB01 is capable of inducing oxidation of thioredoxin 1 and peroxiredoxin 1, while YJB05 fails to induce oxidation of either thioredoxin 1 and peroxiredoxin 1.

SW480 human colon cancer cells were grown following the instructions of American Type Culture Collection (ATCC, Monassas, Va.). Cells were treated with either no peptide, with YBJ01 (at 20 μM and 100 μM), or with YBJ05 (at 100 μM). $10^6$ cells were lysed in 6 mol/L guanidinium chloride, 50 mmol/L Tris/HCL (pH 8.3), 3 mmol/L EDTA, and 0.5% Triton-X-100 containing 50 mmol/L iodoacetic acid. After 30 min at 37° C., the excess idoacetic acid was removed using Microspin G-25 columns (GE Healthcare Life Sciences). Oxidized and reduced thioredxoin was separated by native PAGE. The gel was electroblotted onto a nitrocellulose membrane and probed with thioredoxin antibodies, followed by HRP-conjugated secondary antibody. Bands corresponding to thioredoxin were visualized by ECL.

The oxidized peroxiredoxin 1 (sulphonic-peroxiredoxin, Prx-$O_3$) was detected by using the specific anti-Prx-O3 antibody. Briefly, after SW480 cells were treated with either no peptide, with YBJ01 (at 20 μM and 100 μM), or with YJB05 (at 100 μM) for 1 h, total cell lysates were collected and separated on the SDS-PAGE gel. The gel was electroblotted onto a nitrocellulose membrane and probed with anti-Prx-O3, followed by HRP-conjugated secondary antibody. Bands corresponding to sulphonic-peroxiredoxin were visualized by ECL As shown in FIG. 6B, YJB01 induces the oxidized form of thioredoxin 1. This activity is in contrast to that of YJB05, which failed to induce oxidation of thioredoxin 1. As noted above, YJB05 is ineffective in inhibiting the growth of the cells and inducing apoptosis.

The effect of these two peptides on the oxidized form of peroxiredoxin 1, an enzyme known to be involved in the redox regulation of the cell, was also evaluated. (Hall, A., et al., (2009) Febs J, 276:2469-2477; Aran, M., et al., (2009), Febs J, 276:2478-2493). As shown in FIG. 6B, peptide YJB01 induced the oxidized form of peroxiredoxin. This activity is in contrast to YJB05 which failed to induce oxidation. As noted above, YJB05 is ineffective in inhibiting the growth of the cells and inducing apoptosis.

Figure 7A:
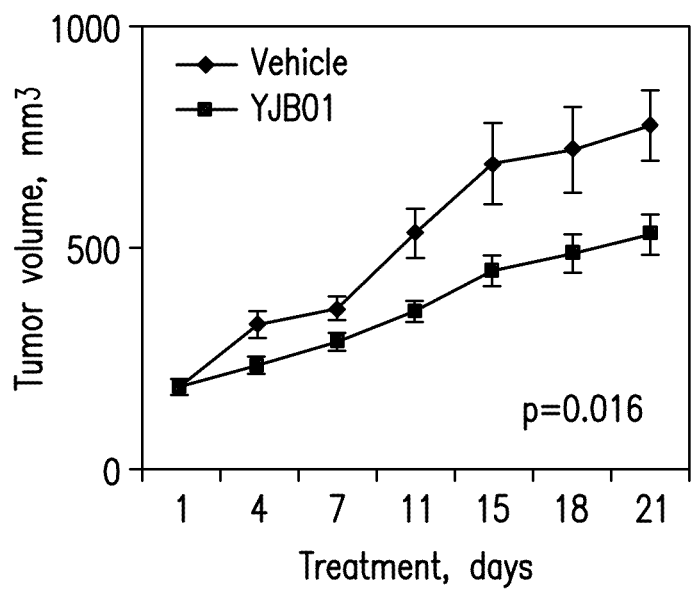
Figure 7B:
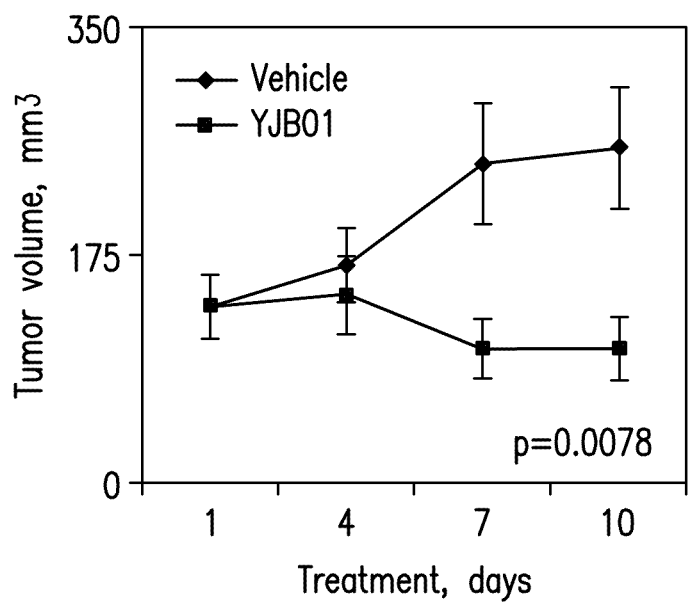

FIGS. 7A-B show that YJB01 is capable of inhibiting the growth of SW480 human colon cancer xenografts in nude mice.

Xenografts were generated as described in FIG. 3A-B and Example 3 except where noted. Each animal had two xenografts, one on its right flank and one on the left. In these studies, the effect of two doses of YJB01, 100 μg and 500 μg per animal were evaluated. The doses were administrated intraperitoneally once a day dissolved in phosphate buffered saline (PBS). Animals receiving the lower dose (3 controls and 4 treated with peptide YJB01) were treated for 21 days as shown in FIG. 7A. Those receiving the higher dose (8 controls and 8 treated with YJB01) were treated for 10 days as shown in FIG. 7B. Control animals were injected with PBS. Tumor volume was determined as described in Example 3. Tumor volume is expressed as mean±SEM. Administration of 100 μg YJB01 for 21 days significantly decreased tumor volume from an average of 776 mm$^3$ in the vehicle group to 527 mm$^3$ in the YJB01 group (p=0.016); this represents a 32% reduction in tumor volume. Administration of 500 μg YJB01 for 10 days significantly decreased tumor volume from and average of 257 mm$^3$ in the vehicle group to 102 mm$^3$ in the YJB01 group (p=0.016) representing a 60% reduction in tumor volume. As shown in FIG. 7B, the higher dose of peptide YJB01 not only inhibited the growth of the tumor compared to control, but also decreased the tumor volume compared to its baseline; in other words, YJB01 caused tumor regression.

FIG. 8 shows the full length nucleotide and amino acid sequences of human thioredoxin (SEQ ID NO:1 and SEQ ID NO:2, respectively). The active site motif of the thioredoxin peptide is indicated by underlining.

Figure 9A:
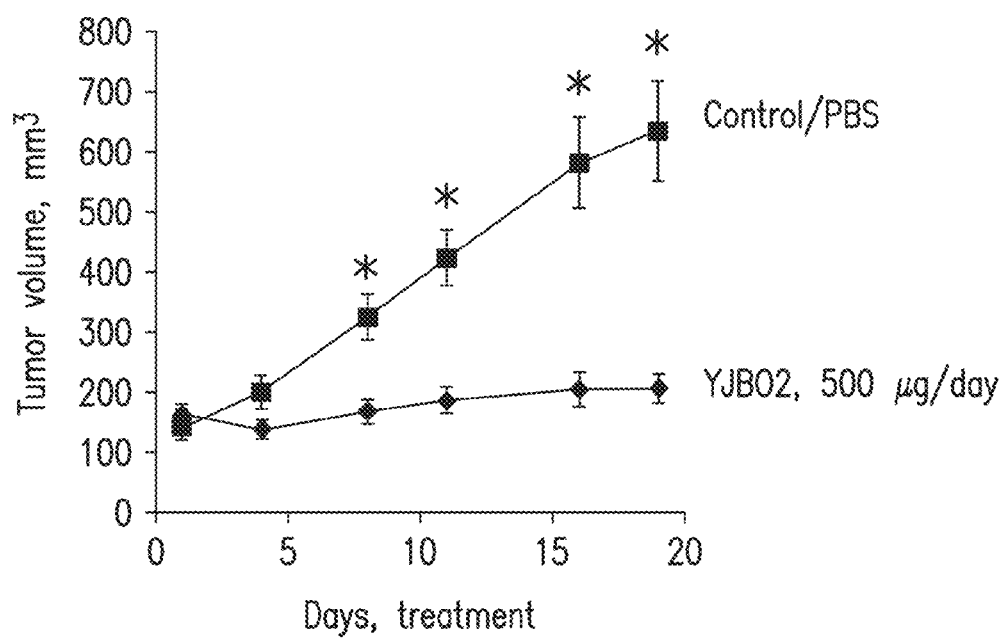
Figure 9B:
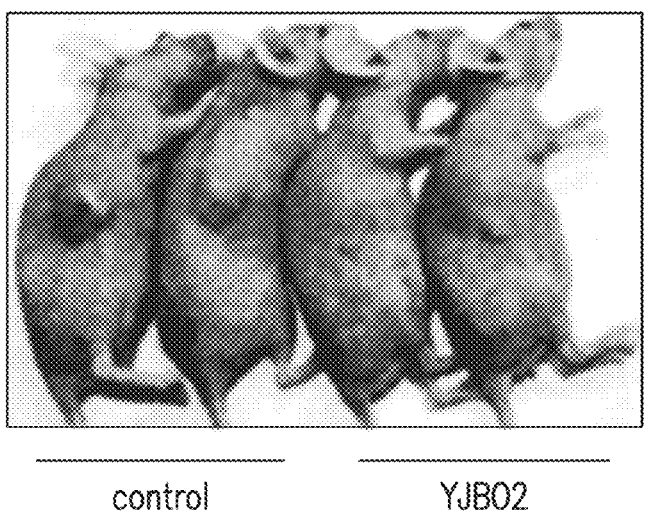

FIGS. 9A-B shows inhibition of SW480 tumor growth by peptide YJB02. Nude mice bearing SW480 (human colon adenocarcinoma cell) xenografts were treated with PBS (control group) or 500 μg/day of YJB02 for 19 days. Tumor volume was monitored and graphed in FIG. 9A. YJB02 inhibited SW480 tumor growth by 67% (207 mm$^3$ vs. 635 mm$^3$ at day 19).

In FIG. 9B, animals were euthanized at day 19 and the mice bearing control or YJB02 treated tumors were photographed. Decreased tumor growth can be seen in the animals treated with YJB02.

Figure 10:
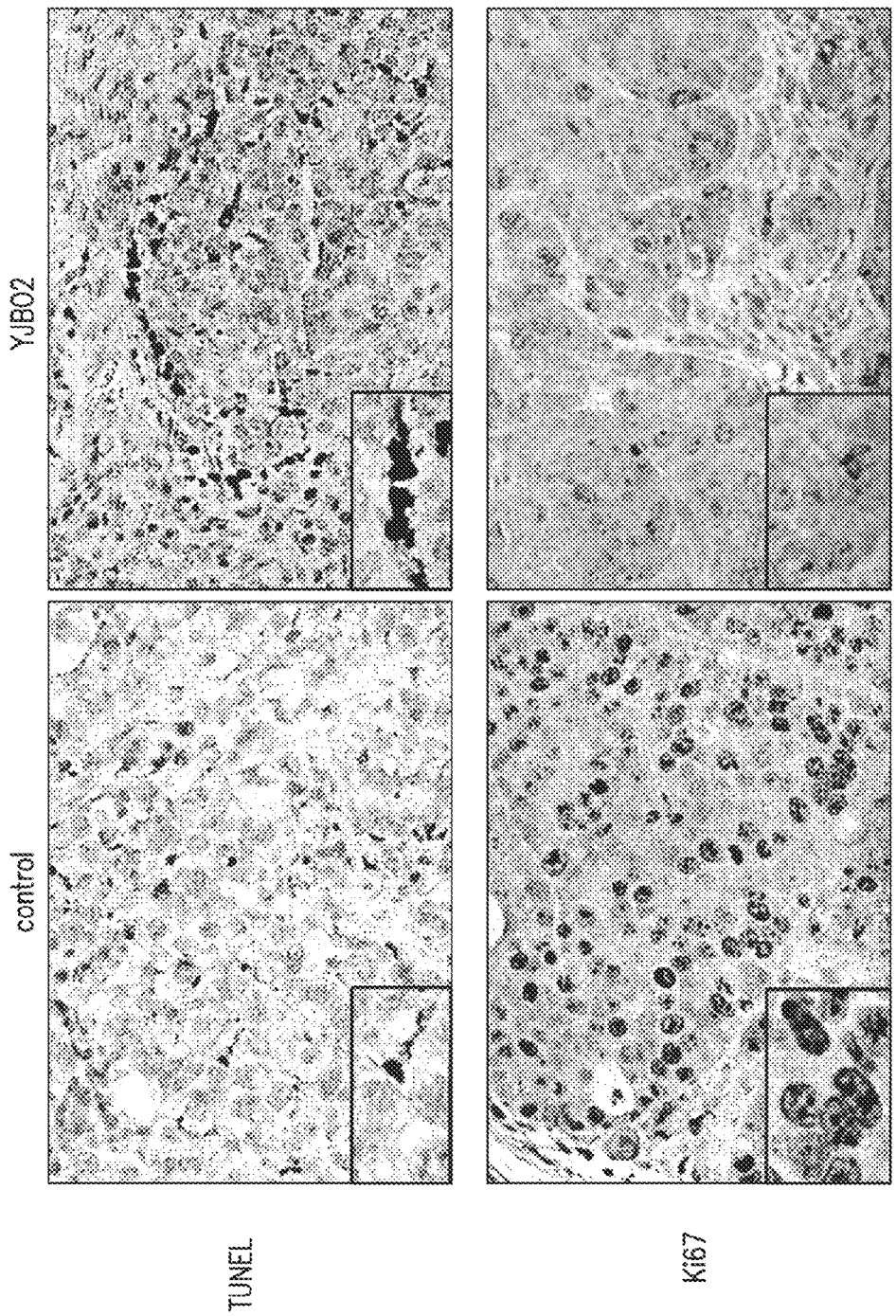

FIG. 10 illustrates that the anti-cancer effect of peptide YJB02 results from induction of apoptosis and inhibition of cell proliferation. Upper panel: Slides were stained with TUNEL kit for apoptosis. YJB02 induced more TUNEL (+) cells than control tumors. Lower panel: YJB02 inhibited tumor cell proliferation. Tissue slides from control or YJB02 treated tumors were stained with anti-Ki67 antibody. The Ki67 (+) signals were dramatically decreased by YJB02. Slides were counter-stained with hematoxylin.

Figure 11:
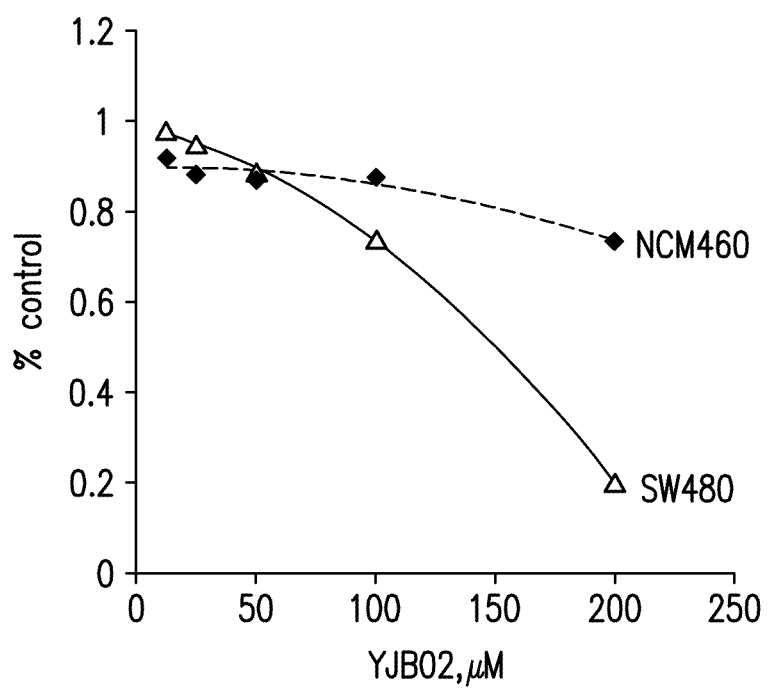

FIG. 11 illustrates specific targeting of malignant cells by peptide YJB02. The effect of YJB02 on colon cancer cells was compared against the effect of YJB302 on the normal human colon epithelial cell line NCM460. After 24-hour treatment with 200 μmol/L YJB02, only 20% SW480 cells remained viable. However, under the same experimental conditions, 75% of NCM460 cells were viable.

Figure 12:
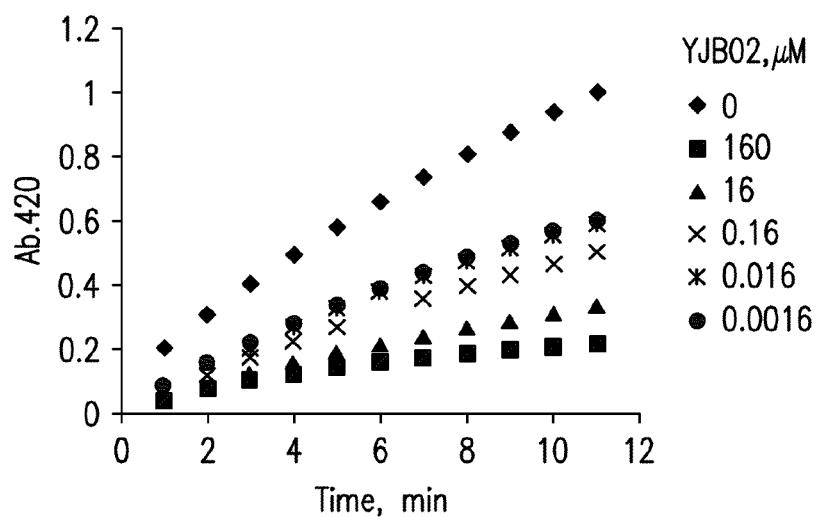

FIG. 12 is an enzyme kinetic graph showing inhibition of thioredoxin reductase activity by peptide YJB02.

DETAILED DESCRIPTION OF THE INVENTION

The present invention provides isolated peptides with at least two cysteine residues capable of forming one or more disulfide bonds. This invention also provides pharmaceutical compositions comprising such peptides as well as methods for inhibiting, preventing, or improving the pathological or clinical manifestations of cancer, inflammatory disorders, neurodegenerative disorders, cardiovascular disorders, or rheumatological disorders via the administration of such peptides.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

A peptide or peptide fragment is "derived from" a parent peptide or polypeptide if it has an amino acid sequence that is homologous to the amino acid sequence of, or is a conserved fragment from, the parent peptide or polypeptide.

As used herein, a cancer or other disease or disorder, e.g., an inflammatory disease or disorder, is "inhibited" if at least one symptom of the cancer or other disease is alleviated, treated, terminated, slowed, or prevented or other manifestations of the disease such as pre-symptomatic findings, such as, for example, changes in joint structure and/or relevant radiological or biochemical findings are ameliorated. As used herein, cancer is also "inhibited" if the occurrence or recurrence of cancer is prevented or delayed or metastasis of the cancer is reduced, slowed, delayed, or prevented. The term "treat" when used with reference to treating, e.g., a pathology or disease, refers to the mitigation and/or elimination of one or more symptoms or other clinical or laboratory manifestations, such as radiological or biochemical changes of that pathology or disease, and/or a reduction in the rate of onset or severity of one or more symptoms or other clinical or laboratory manifestations, such as radiological or biochemical changes of that pathology or disease, and/or the prevention of that pathology or disease.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

"Isolated," when used to describe the various peptides or proteins disclosed herein, means peptide or protein that has been identified and separated and/or recovered from a component of its natural environment. Contaminant components of its natural environment are materials that would typically interfere with diagnostic or therapeutic uses for the peptide or protein, and may include enzymes, hormones, and other proteinaceous or nonproteinaceous solutes.

Various aspects of this disclosure are described in further detail in the following subsections.

Peptides of this Disclosure

The peptide compositions of the present invention contain at least two cysteine residues in proximity such that one or more disulfide bridges can be formed. The inhibitory peptide can comprise additional amino acid residues between the two cysteine residues and can comprise additional amino acid residues flanking the cysteine residues, e.g., amino acid residues which facilitate transport of the peptide into the cell.

In one embodiment, the peptide has the sequence:

$$Y_1\text{-}(x)n\text{-}Cys\text{-}(y)N\text{-}Cys\text{-}(z)n\text{-}Y_2$$

wherein:

x, y, and z=any amino acid;

n=any number;

N=any number that allows formation of one or more intramolecular disulfide bonds;

$Y_1$ is hydrogen or an amino-derivative group and $Y_2$ is hydrogen or a carboxy-derivative group;

wherein an intramolecular disulfide bond is formed between the two cysteine.

In certain embodiments, the peptide includes additional cysteine residues and intramolecular disulfide bonds.

Preferably, the peptide is about 4-35 amino acids in length. More preferably, the peptide is about 6-26 amino acids in length. More preferably, the peptide is about 6-25 amino acids in length. Even more preferably, the peptide is about 8-20 amino acids in length. In another embodiment, the peptide can be any length that allows the peptide to retain its inhibitory activity.

In certain embodiments of the invention, (y)N is comprises a sequence selected from the group consisting of: Gly-Pro, Ser-Tyr, Gly-His, Pro-His, and Pro-(0 to 118 amino acids)-Val.

In additional embodiments, peptide compounds of the invention are derived from the active site motif of thioredoxin, which contains two cysteine residues which form a disulfide bridge. The complete nucleotide and amino acid sequences of human thioredoxin (GenBank Accession No. NM_003329) are shown in SEQ ID NOs: 1 and 2, respectively, and in FIG. 8. The peptide compositions of the invention are not limited to peptides comprising the active site motif of human thioredoxin. For example, in alternative embodiments, a peptide of the invention comprises or consists of the active site of thioredoxin, glutaredoxin, thioredoxin reductase, protein disulfide isomerase, disulfide interchange protein DsbA, or peroxiredoxin, as set forth in FIG. 1B, or modified versions of these active sites, e.g., where the length of the active site motif has been altered or where there has been amino acid substitutions. For example, a peptide of the invention may comprise the entire active site of thioredoxin (-Trp-Cys-Gly-Pro-Cys-Lys; SEQ ID NO:4), or a portion or fragment thereof.

Exemplary peptides of this invention include, but are not limited to, YJB01, which is a 25 amino acid peptide and is set forth in SEQ ID NO:9 and FIG. 1A; YJB02, which is a 26 amino acid peptide and is set forth in SEQ ID NO:10 and FIG. 1A; YJB03, which is a 23 amino acid peptide and is set forth in SEQ ID NO:11 and FIG. 1A; YJB04, which is a 24 amino acid peptide and is set forth in SEQ ID NO: 12 and FIG. 1A; YJB07, which is a 21 amino acid peptide and is set forth in SEQ ID NO:13 and FIG. 1A; and YJB08, which is a 21 amino acid peptide and is set forth in SEQ ID NO:14 and FIG. 1A.

The peptide YJB01 contains eight amino acids of human thioredoxin (residues A29 to $K_{36}$ of the full length thioredoxin sequence SEQ ID NO:2). These eight amino acids include the thioredoxin active site motif (-Trp-Cys-Gly-Pro-Cys-Lys; SEQ ID NO:3). The active site motif of thioredoxin contains two cysteine residues as well as a disulfide bridge. The remaining 16 amino acids of YJB01 (residues P9 to K25 of SEQ ID NO:9) facilitate its access into the cell. YJB02 (SEQ ID NO:10) contains the six amino acids of the thioredoxin reductase active site (SEQ ID NO:5) and the same 16 amino acids as YJB01 to facilitate access into the cell. YJB03 (SEQ ID NO:11) is based on the four amino acid active site sequence of glutaredoxin (SEQ ID NO:4) and contains the same 16 amino acids as YJB01 to facilitate access into the cell. YJB04 (SEQ ID NO:12) is based on a truncated version of the active site of peroxiredoxin (SEQ ID NO:8) and also contains the same 16 amino acids as YJB01 to facilitate access into the cell. YJB07 (SEQ ID NO:13) contains the four amino acid active site sequence of protein disulfide isomerase (SEQ ID NO:6), as well as the same 16 amino acids as YJB01 to facilitate access into the cell. YJB08 (SEQ ID NO:14) contains the four amino acid active site sequence of disulfide interchange protein DsbA (SEQ ID NO:7) and the same 16 amino acids as YJB01 to facilitate access into the cell.

In addition to peptide compounds that comprise an amino acid sequence that is identical to the active site of native thioredoxin or the active site of glutaredoxin, thioredoxin reductase, protein disulfide isomerase, disulfide interchange protein DsbA, or peroxiredoxin, the invention also encompasses peptide compounds that are "substantially similar" to one of these active sites. Peptide compounds described herein as being "substantially similar" to a particular region of a reference protein (e.g., a region containing at least two cysteine amino acid residues and forming a disulfide bond) include peptides that retain certain structural and functional features of the native peptide yet differ from the native amino acid sequence within the particular region at one or more amino acid position (i.e., by amino acid substitutions). For example, a peptide that is substantially similar to a native thioredoxin peptide retains the ability to inhibit the growth of tumor cells or cause regression of tumor cells.

Peptides altered from the native sequence can be prepared by substituting amino acid residues within a native peptide and selecting peptides with the desired inhibitory activity. For example, amino acid residues of the thioredoxin peptide active site (or any of the active sites identified in FIG. 1B) can be systematically substituted with other residues and the substituted peptides can then be tested in standard assays for evaluating the effects of such substitutions on the ability of the peptide to inhibit tumor cell growth or induce regression of such tumors. In some embodiments, to retain functional activity, conservative amino acid substitutions are made. As used herein, the language a "conservative amino acid substitution" is intended to include a substitution in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptides can be prepared by standard techniques, such as automated chemical synthesis, as described further above.

The effect of the amino acid substitutions on the ability of the peptide to inhibit tumor cell growth or to induce tumor regression is tested in standard assays as well-known in the art and described herein (see, for example, Examples 2 and 3).

In one embodiment, a peptide of the present invention is at least about 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, homologous to the amino acid sequence of a peptide selected from the group consisting of YJB01, YJB02, YJB03, YJB04, YJB07, and YJB08, wherein the peptide contains at least two cysteine residues capable of forming one or more disulfide bridges.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases, for example, to identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See the National Center for Biotechnology Information (NCBI) website.

Peptide compounds of the invention can be prepared by any suitable method for peptide synthesis, including chemical synthesis and recombinant DNA technology. Preferably, the peptides are chemically synthesized. Methods for chemically synthesizing peptides are well known in the art (see e.g., Bodansky, M. Principles of Peptide Synthesis, Springer Verlag, Berlin (1993) and Grant, G. A (ed.). Synthetic Peptides: A User's Guide, W.H. Freeman and Company, New York (1992). Automated peptide synthesizers are commercially available (e.g., Advanced ChemTech Model 396; Milligen/Biosearch 9600). Methods for preparing peptides by recombinant expression in a host cell of DNA encoding the peptide are also well known in the art (see e.g., Sambrook et al., (1989) Molecular Cloning: A Laboratory Manual, 2nd Edition, Cold Spring Harbor Laboratory Press).

In addition to amino acid-substituted peptides, the invention also encompasses peptide compounds having other modifications. For example, the amino-terminus or carboxyterminus of the peptide can be modified. The language "amino-derivative group" is intended to include amino-terminal modifications of the peptide compounds of the invention. Examples of N-terminal modifications include alkyl, cycloalkyl, aryl, arylalkyl, and acyl groups. A preferred N-terminal modification is acetylation. The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylakanoyl, arylaminocarbonyl, alkylaminocarbonyl, cycloalkylaminocarbonyl, alkyloxycarbonyl (carbamate caps), and cycloalkoxycarbonyl, among others.

The language "carboxy-derivative group" is intended to include carboxy-terminal modifications of the peptide compounds of the invention. Examples of modifications of the C-terminus include modification of the carbonyl carbon of the C-terminal residue to form a carboxyterminal amide or alcohol (i.e., as reduced form). In general, the amide nitrogen, covalently bound to the carbonyl carbon on the C-terminal residue, will have two substitution groups, each of which can be hydrogen, alkyl or an alkylaryl group (substituted or unsubstituted). Preferably the C-terminal is an amido group, such as —$CONH_2$, —$CONHCH_3$, —$CONHCH_2C_6H_5$ or —$CON(CH_3)_2$, but may also be 2-, 3-, or 4-pyridylmethyl, 2-, 3-, or 4-pyridylethyl, carboxylic acid, ethers, carbonyl esters, alkyl, arylalkyl, aryl, cyclohexylamide, piperidineamide and other mono or disubstituted amides. Other moieties that can be linked to the C-terminal residue include piperidine-4-carboxylic acid or amide and cis- or trans-4-amino-cyclohexanecarboxylic acid or amide.

Moreover, modification of one or more side chains of noncritical amino acid residues (e.g., "neutral" residues) may be tolerated without altering the function of the peptide. A covalent modification of an amino acid side chain or terminal residue may be introduced into the peptide by reacting targeted amino acid residues of the peptide with an organic derivative agent that is capable of reacting with selected side chains or terminal residues. Examples of typical side chain modifications are described further below.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloro-mercuribenzoate, 2-chloromercuri-4-nitrophenol, or chloro-7-nitrobenzo-2-oxa-1,3-diazole. Cysteinyl residues can also react with nitric oxide generating three potential derivatives, sulphenic (SOH), sulphinic ($SO_2^-$) and sulphonic ($SO_3^-$), with progressively increasing chemical stability, the last one representing an irreversible change. Such derivatives can occur in vivo and can also be synthesized in vitro (Hess et al., (2005) *Nat Rev Mol Cell Biol.* 6:150-66).

Histidyl residues are derivatized by reaction with diethylpyrocarbonate at pH 5.5-7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imodoesters such as methyl picolinimidate; pyridoxal phosphate; pyridoxal; chloroborohydride; trinitobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents can react with the groups of lysine as well as the arginine epsilon-amino groups.

The specific modification of tyrosyl residues per se has been studied extensively, with particular interest in introducing spectral labels into tyrosyl residues by reaction with aromatic diazonium compounds or tetranitromethane. Commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N═C═N—R') such as 1-cyclohexyl-3-(2-morpholinyl-(4-ethyl) carbodiimide or 1-ethyl-3-(4-azonia-4,4-demethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton (1983) Proteins: Structure and Molecular Properties, W.H. Freeman & Co., San Francisco, pp. 79-86).

The activity of covalently modified peptides (e.g., endterminal or side chain modified peptides) can be evaluated in the direct T cell stimulation assay and/or the competitive inhibition assay, described above.

As used herein, the terms "peptide," "peptide compound," and "peptidic compound" are intended to include peptides comprised of naturally-occurring amino acids, as well as peptide derivatives, peptide analogues and peptide mimetics of the naturally-occurring amino acid structures. The terms "peptide analogue", "peptide derivative" and "peptidomimetic" as used herein are intended to include molecules which mimic the chemical structure of a peptide and retain the functional properties of the peptide. Approaches to designing peptide analogues, derivatives and mimetics are known in the art. For example, see Farmer, P. S., in Drug Design (E. J. Ariens, ed.) Academic Press, New York, 1980, vol. 10, pp. 119-143; Ball, J. B., and Alewood, P. F., (1990) *J. Mol. Recognition*. 3:55; Morgan, B. A., and Gainor, J. A., (1989) *Ann. Rep. Med. Chem.* 24:243; and Freidinger, R. M. (1989) *Trends Pharmacol. Sci.* 10:270.

As used herein, a "derivative" of a compound X (e.g., a peptide or amino acid) refers to a form of X in which one or more reactive groups on the compound have been derivatized with a modifying (derivative) group. Examples of peptide derivatives include peptides in which an amino acid side chain, the peptide backbone, or the amino- or carboxy-terminus has been derivatized (e.g., peptidic compounds with methylated amide linkages).

An "analogue" of a reference amino acid, as the term is used herein, is an α- or β-amino acid having a side chain which is (a) the same as the side chain of the reference amino acid (when the analogue is a β-amino acid residue, a peptide, or the D-amino acid enantiomer of the reference acid); (b) is an isomer of the side chain of the reference amino acid; (c) is a homologue of the side chain of the reference amino acid; (d) results from replacement of a methylene group in the side chain of the reference amino acid with a heteroatom or group selected from NH, O and S; (e) results from a simple substitution on the side chain of the reference amino acid or any of the preceding (a) to (c); and/or (f) results from a conservative substitution (discussed infra). Analogues of a reference amino acid further include the reference amino acid or any of (a)-(e) above in which the α-nitrogen atom is substituted by a lower alkyl group, preferably a methyl group. A "homologue" of the given amino acid is an α- or β-amino acid having a side chain which differs from the side chain of the given amino acid by the addition or deletion of from 1 to 4 methylene groups. A "simple substitution" of an amino acid side chain results from the substitution of a hydrogen atom in the side chain of the given amino acid with a small substituent, such as a lower alkyl group, preferably a methyl group; a halogen atom, preferably a fluorine, chlorine, bromine or iodine atom; or hydroxy.

"Peptide mimetics" that are structurally similar to therapeutically useful peptides may be used to produce an equivalent therapeutic or prophylactic effect. The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Generally, peptidomimetics are structurally similar to a paradigm peptide (i.e., a peptide that has a biological or pharmacological activity), but have one or more peptide linkages optionally replaced by a linkage such as: —CH₂NH—, —CH₂S—, —CH₂—CH₂—, —CH═CH—(cis and trans), —COCH₂—, —CH(OH)CH₂—, and —CH₂SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci. pp.* 463-468 (general review); Hudson, D. et al., (1979) *Int. J. Pept. Prot. Res.* 14:177-185 (—CH2NH—, CH2CH2-); Spatola, A. F. et al., (1986) *Life Sci.* 38:1243-1249 (—CH2-S); Hann, M. M., (1982) *J. Chem. Soc. Perkin Trans.* 1307-314 (—CH═CH—, cis and trans); Almquist, R. G. et al. (1980) *J. Med. Chem.* 23:1392-1398 (—COCH2-); Jennings-White, C. et al., (1982) *Tetrahedron Lett.* 23:2533 (—COCH2-); Szelke, M. et al., European Appln. EP 45665 (1982) *CA*: 97:39405 (1982)(—CH(OH)CH2-); Holladay, M. W. et al., (1983) *Tetrahedron Lett.* 24:4401-4404 (—C(OH)CH2-); and Hruby, V. J., (1982) *Life Sci.* 31:189-199 (—CH₂—S—); each of which is incorporated herein by reference. A particularly preferred non-peptide linkage is —CH₂NH—.

Other examples of isosteres include peptides substituted with one or more benzodiazepine molecules (see, e.g., James, G. L. et al. (1993) *Science* 260:1937-1942). Other possible modifications include an N-alkyl (or aryl) substitution, backbone crosslinking to construct lactams and other cyclic structures, substitution of all D-amino acids for all L-amino acids within the compound ("inverso" compounds) or retro-inverso amino acid incorporation. By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al., (1981) *Perspectives in Peptide Chemistry* pp. 283-294. See also U.S. Pat. No. 4,522, 752 by Sisto for further description of "retro-inverso" peptides. Other derivatives include C-terminal hydroxymethyl derivatives, O-modified derivatives (e.g., C-terminal hydroxymethyl benzyl ether) and N-terminally modified derivatives including substituted amides such as alkylamides and hydrazides.

Such peptide mimetics may have significant advantages over peptide embodiments, including, for example: more economical production, greater chemical stability, enhanced pharmacological properties (e.g., half-life, absorption, potency, efficacy, and the like), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of an amino acid sequence with a D-amino acid of the same type (e.g., D-lysine in place of L-lysine) may be used to generate more stable peptides. In addition, constrained peptides may be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

Nucleic Acid Molecules Encoding Peptides of this Disclosure

Another aspect of this disclosure pertains to isolated nucleic acid molecules that encode the peptides of this disclosure, and portions thereof, as well as complements of such nucleic acid molecules. The nucleotide sequence of human thioredoxin is set forth in FIG. 8 and in SEQ ID NO:1.

In other embodiments, the nucleic acid molecule of the invention is sufficiently complementary to a nucleotide sequence encoding a peptide of this disclosure such that it can hybridize to a nucleotide sequence encoding a peptide of this disclosure, thereby forming a stable duplex. In another embodiment, an isolated nucleic acid molecule of the present invention includes a nucleotide sequence which is at least about: 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, or more homologous to a nucleotide sequence encoding a peptide of this disclosure, or a portion, preferably of the same length, of any of these nucleotide sequences.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Recombinant expression vectors which include the nucleic acids of the invention, and host cells transfected with such vectors, are also provided.

As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses. The expression vector can be a yeast expression vector, a vector for expression in insect cells, e.g., a baculovirus expression vector or a vector suitable for expression in mammalian cells.

The recombinant expression vectors of the invention can be designed for expression of the peptides of the invention in prokaryotic or eukaryotic cells. For example, peptides of the invention can be expressed in *E. coli*, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

The term "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein. A host cell can be any prokaryotic or eukaryotic cell.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a peptide of the invention. Accordingly, the invention further provides methods for producing a peptide of the invention using the host cells of the invention. In one embodiment, the method includes culturing the host cell of the invention (into which a recombinant expression vector encoding a peptide of the invention has been introduced) in a suitable medium such that a peptide of the invention is produced. In another embodiment, the method further includes isolating a peptide of the invention from the medium or the host cell.

Uses and Methods of this Disclosure

Cancer

In one aspect, the present invention relates to treatment of a subject in vivo using a peptide of the invention such that growth of cancerous tumors is inhibited. A peptide of the invention can be used alone to inhibit or to prevent the growth of cancerous tumors or to cause them to regress. For example, tumor growth can be inhibited by induction of apoptosis and/or inhibition of cell proliferation. Alternatively, a peptide of the invention can be used in conjunction with other chemotherapeutic agents such as immunogenic agents, standard cancer treatments, etc., as described below.

Accordingly, in one embodiment, the invention provides a method of inhibiting or preventing the growth of tumor cells or inducing tumor regression in a subject, including administering to the subject a therapeutically effective amount of a peptide of the invention.

As used herein, the term "cancer" refers to cells having the capacity for autonomous growth, i.e., an abnormal state or condition characterized by rapidly proliferating cell growth, as well as cancer stem cells that possess characteristics associated with normal stem cells, specifically the ability to give rise to all cell types found in a particular cancer sample. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness.

Non-limiting examples of preferred cancers for treatment include colon cancer, pancreatic cancer, and breast cancer. Additionally, the invention includes refractory or recurrent malignancies whose growth can be inhibited using the peptides of the invention.

Examples of other cancers that may be treated using the peptides of the invention include melanoma (e.g., metastatic malignant melanoma), renal cancer (e.g. clear cell carcinoma), prostate cancer (e.g. hormone refractory prostate adenocarcinoma), lung cancer, bone cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers.

A peptide of the invention can be combined with standard cancer treatments and chemotherapeutic regimes. In these instances, a reduction in the dose of the chemotherapeutic reagent administered is possible. (Mokyr, M. et al., (1998) *Cancer Research* 58: 5301-5304).

A "chemotherapeutic agent" is a chemical compound useful in the treatment of cancer. Examples of chemotherapeutic agents include standard anti-cancer agents such as alkylating agents, topoisomerase I inhibitors, topoisomerase II inhibitors, RNA/DNA antimetabolites, DNA antimetabolites, antimitotic agents and others (see below in detail). Alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma and calicheamicin phi, see, e.g., Agnew, *Chem. Intl. Ed. Engl.,* 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-Lnorleucine, doxorubicin (Adriamycinrn) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (S-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; Ionidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK; razoxane; rhizox in; sizofuran; spirogermanium; tenuazonic acid; triaziquone; 2, 2',2"-trichlorotriethylamine; trichothecenes (especially T-2 toxin, verracurin A, roridin A and anguidine); urethan; 5 vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL, Bristol-Myers Squibb Oncology, Princeton, N.J.) and doxetaxel (TAXOTERE, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine); novantrone; teniposide; edatrexate; daunomycin; aminopterin; xeloda; ibandronate; CPT-II; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as antiestrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4 (5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

Other combination therapies that can result in synergy with a peptide of the invention are radiation and surgery. Angiogenesis inhibitors can also be combined with a peptide of the invention.

Optionally, a peptide of the invention can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28).

In certain instances, a peptide of the invention can be more effective when combined with a vaccination protocol. Many experimental strategies for vaccination against tumors have been devised (see Rosenberg, S., (2000) Development of Cancer Vaccines, ASCO Educational Book Spring: 60-62; Logothetis, C., (2000) *ASCO Educational Book Spring:* 300-302; Khayat, D., (2000) ASCO Educational Book Spring: 414-428; Foon, K., (2000) ASCO Educational Book Spring: 730-738; see also Restifo, N. and Sznol, M., Cancer Vaccines, Ch. 61, pp. 3023-3043 in DeVita, V. et al. (eds.), (1997) Cancer: Principles and Practice of Oncology. Fifth Edition). In one of these strategies, a vaccine is prepared using autologous or allogeneic tumor cells. These cellular vaccines have been shown to be more effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

In another example, a peptide of the invention can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like.

Inflammatory Diseases or Disorders

As used herein, an "inflammatory disorder" is intended to include a disease or disorder characterized by, caused by, resulting from, or becoming affected by inflammation. An inflammatory disorder can be caused by or be associated with biological and pathological processes associated with, for example, a redox-mediated processes. Accordingly, the RONS-generating peptides of the instant invention can be employed to inhibit, prevent, or improve the pathological or clinical manifestations of such disorders.

Examples of inflammatory disorders include, but are not limited to, acute and chronic inflammatory disorders such as asthma, psoriasis, rheumatological diseases such as, for example, rheumatoid arthritis, osteoarthritis, psoriatic arthritis, inflammatory bowel disease (Crohn's disease, ulcerative colitis), ankylosing spondylitis, sepsis, vasculitis, and bursitis; autoimmune diseases such as Lupus, Polymyalgia, Rheumatica, Scleroderma, Wegener's granulomatosis, temporal arteritis, cryoglobulinemia, and multiple sclerosis; transplant rejection; osteoporosis; neurodegenerative diseases such as Alzheimer's disease; cardiovascular diseases, such as coronary artery disease (CAD), atherosclerosis; viral (e.g., HIV or influenza) infections; chronic viral (e.g., Epstein-Barr, cytomegalovirus, herpes simplex virus) infection; and ataxia telangiectasia.

Pathological processes associated with a pro-inflammatory response in which the peptides of the invention would be useful for treatment further include allergies such as joint diseases, allergic rhinitis, uticaria, anaphylaxis, drug sensitivity, food sensitivity and the like; cutaneous inflammation such as dermatitis, eczema, psoriasis, contact dermatitis, sunburn, aging, and the like; arthritis such as osteoarthritis, psoriatic arthritis, lupus, spondylarthritis and the like; chronic obstruction pulmonary disease and chronic inflammatory bowel disease.

Pharmaceutical Compositions

Pharmaceutical compositions of this disclosure also can be administered in combination therapy, i.e., combined with other agents. For example, the combination therapy can include a peptide of the present disclosure combined with at least one additional anti-cancer or anti-inflammatory agent. Examples of therapeutic agents that can be used in combination therapy are described in greater detail above.

The peptide compounds of the invention can be formulated into compositions suitable for pharmaceutical administration. The pharmaceutical composition typically includes a peptide (or modified form thereof as described above) and a pharmaceutically acceptable carrier.

The peptides of the invention can be administered alone or linked to a carrier peptide, e.g., a cell penetrating peptide such as the Tat carrier peptide, to facilitate access into cells. Other suitable cell penetrating peptides are known and contemplated, such as the *Drosophila* Antennapedia homeodomain (Theodore et al., (1995) *J. Neurosci.* 15:7158; Johnson, et al., (1996) *Circ. Res.* 79:1086), wherein the peptide is cross-linked via an N-terminal Cys-Cys bond to the Antennapedia carrier. Polyarginine is another exemplary cell penetrating peptide (Mitchell et al., (2000) J. Peptide Res., 56:318-325; Rothbard et al., (2000) *Nature Med.,* 6:1253-1257).

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL. (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (i.e., the peptide or derivative thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to tumor cells with monoclonal antibodies to tumor antigens) can also be used as pharmaceutically acceptable carriers. These may be prepared according to methods known to those skilled in the art, for example, as described in U.S. Pat. No. 4,522,811, and International Patent Application Serial PCT/US94/07327. For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of invariant chain protein or peptide is then introduced into the container. The container is then swirled by hand to free lipid material from the sides of the container and to disperse lipid aggregates, thereby forming the liposomal suspension.

Pharmaceutical compositions, including, but not limited to, such liposomal suspensions and other microencapsulated compositions, can be combined with targeting agents to allow for tissue or tumor specific delivery of the peptides of the invention. Such targeting can be achieved, by way of example, and not by way of limitation, through the use of tissue and/or tumor specific antibodies and antibody mimetics. Exemplary antibody mimetics include molecules such as Affibodies, DARPins, Anticalins, Avimers, and Versabodies, all of which employ binding structures that, while they mimic traditional antibody binding and therefore can be used to target peptides to tissues specifically expressing the antigen recognized by the mimetic, are generated from and function via distinct mechanisms.

Pharmaceutical compositions may also be prepared wherein the peptide of the invention is covalently or non-covalently attached to a nanoparticle. By way of example, but not limitation, a nanoparticle can be a dendrimer, such as the polyamidoamine employed in Kukowska-Latallo et al., (2005) *Cancer Res.*, vol. 65, pp. 5317-24, which is incorporated herein by reference in its entirety. Other dendrimers that can be used in conjunction with the peptides of the instant invention include, but are not limited to, Polypropylenimine dendrimers as described in U.S. Pat. No. 7,078,461, which is hereby incorporated by reference in its entirety.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a peptide of this disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth or induces tumor regression by at least about 10%, or more preferably by at least about 20%, more preferably by at least about 40%, even more preferably by at least about 60%, and still more preferably by at least about 80% relative to untreated subjects.

Animal models accepted in the art as models of human cancer or inflammatory disease can be used to test particular peptide compounds, routes of administration etc., to determine appropriate amounts of the peptide compounds of the invention.

The ability of a compound to inhibit tumor growth or induce tumor regression can be evaluated in an animal model system predictive of efficacy in human tumors. Alternatively, this property of a composition can be evaluated by examining the ability of the compound to inhibit cell growth in cancer cells and/or cancer stem cells, such inhibition can be measured in vitro by assays known to the skilled practitioner and described herein, e.g., Examples 2 and 4-6, below. A therapeutically effective amount of a therapeutic compound can decrease tumor size, prevent the tumor from further growth or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Routes of administration for peptides of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a peptide of this disclosure can be administered via a non-parenteral route, such as a topical, epidermal or mucosal route of administration, for example, intranasally, orally, vaginally, rectally, sublingually or topically.

Therapeutic compositions can be administered with medical devices known in the art. For example, in a preferred embodiment, a therapeutic composition of this disclosure can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The present invention is further illustrated by the following examples which should not be construed as further limiting.

The contents of all figures and all references, patents and published patent applications and Accession numbers cited throughout this application are expressly incorporated herein by reference.

EXAMPLES

Example 1

Peptide Synthesis

This example describes the synthesis of peptides useful in the methods of the invention, including those based on the structure of the active site of thioredoxin, glutaredoxin, and thioredoxin reductase, protein disulfide isomerase, disulfide interchange protein DsbA, and peroxiredoxin. Peptides were synthesized first with Solid-Phase Peptide Synthesis (SPPS) of a linear peptide carried out on acid-labile resin. Solid-phase peptide elongation was then carried out by using Fmoc protection scheme, with a 20-min de-protection step with piperidine/DMF and a variable coupling time with Fmoc amino acid/DIC/HOBT with preactivation. The completion of the amino acid coupling reaction was determined by the ninhydrin test. The linear peptide was then cleaved off the resin with 20% TFE (trifluoroethanol) in DCM, and an appropriate cleavage cocktail was used to remove the side chain protecting groups. The peptide was further purified by conventional HPLC method using reverse C18 column and a gradient of acetonitrile in aqueous buffer solutions. The purified peptide was dried by lyophilization and characterized by analytical HPLC and mass spectrometry analysis. After the purification, the linear peptide was dissolved in DI water and cyclized in air for more than 36 hours. After cyclization, the peptide was purified again to the desired purity (95% in this case). The purified peptide was dried by lyophilization and characterized by analytical HPLC and mass spectrometry analysis.

Six peptides were synthesized, as shown in the FIG. 1A, including peptides based on the structure of the active site of thioredoxin (-Trp-Cys-Gly-Pro-Cys-Lys-) (SEQ ID NO:3), glutaredoxin (-Cys-Ser-Tyr-Cys-) (SEQ ID NO:4), thioredoxin reductase (-Cys-Val-Asn-Val-Gly-Cys-) (SEQ ID NO:5.), protein disulfide isomerase (-Cys-Gly-His-Cys-) (SEQ ID NO:6), disulfide interchange protein DsbA (-Cys-Pro-His-Cys-) (SEQ ID NO:7), and peroxiredoxin (-Val-Cys-Pro-(118 amino acids)-Val-Cys-Pro-) (SEQ ID NO:8). In particular, the YJB01 peptide contains eight amino acids of thioredoxin (underlined) which represent amino acid residues A29 to K36, including C32 and C35 (bolded), of the human thioredoxin protein (full length sequence provided as SEQ ID NO:2, active site sequence provided as SEQ ID NO:3). YJB01 also contains 16 additional amino acids (residues P9 through K25 of SEQ ID NO:9) which facilitate its access into the cell. FIG. 1A also shows YJB02 (SEQ ID NO:10), which contains the six amino acids of the thioredoxin reductase active site and the same 16 amino acids as YJB01 to facilitate access into the cell; YJB03 (SEQ ID NO:11), which is based on the four amino acid active site sequence of glutaredoxin; YJB04 (SEQ ID NO:12), which is based on a truncated version of the active site of peroxiredoxin; YJB07 (SEQ ID NO:13), which contains the four amino acid active site sequence of protein disulfide isomerase; and YJB08 (SEQ ID NO:14), which contains the four amino acid active site sequence of disulfide interchange protein DsbA. FIG. 1A also shows YJB05 (SEQ ID NO:15), a control peptide where the two bolded cysteines from YJB01 have been replaced by two alanines, and YJB06 (SEQ ID NO:16) a control peptide where amino acids K8-K25 of YJB01, including the sequence employed to facilitate access into the cell have been deleted.

Example 2

In vitro Cell Viability Assay by MTT

This example describes inhibition of human colon, pancreatic, and breast cancer cell growth in vitro by the anticancer peptides YJB01, YJB02, YJB03, and YJB04 using cultured human colon (HT29 and SW480 cells), pancreatic (BxPC3), and breast (MCF7 and MDA-MB-231) cancer cells.

10,000 HT29 or SW480 human colon cancer cells, BxPC-3 human pancreatic cancer cells, and MCF7 and MDA-MB-231 breast cancer cells were obtained from American Type Culture Collection (ATTC), Manassas, Va., and were seeded in separate 96-well plates. After treatment with various concentrations (6.25 µM, 12.5 µM, 25 µM, 50 µM, 100 µM, or 200 µM) of test peptide for 24 h, cells were stained with MTT (3-(4,5-Dimethyl-2-thiazolyl)-2,5-diphenyl-2H-tetrazolium bromide, from Sigma-Aldrich) following the instructions of the manufacturer. Before dissolving MTT in SDS, the HT29 and SW480 cells were photographed using a digital camera connected with a phase-contrast microscope. (FIG. 2A1-8, and FIG. 2B1-6). Cells that are alive convert MTT into formazan in their active mitochondria and appear dark purple; dead cells are not stained by MTT and appear colorless.

Two control experiments were also performed by pre-treating the YJB01 peptide with 1 mM DTT to reduce the disulfide bond (see FIG. 2A2-4, and FIG. 2B2-4). Treatment with YJB01 showed markedly diminished inhibition of cell growth, in general over 80% (see FIGS. 2A7 and 2A8 for HT29 cells and FIGS. 2B5 and 2B6 for SW480 cells).

The $IC_{50}$s in HT29, SW480, BxPC3, MCF7, and MDA-MB-231 cell lines, as shown below in Table 1, were measured to show inhibition of cell growth in vitro. The $IC_{50}$ is the concentration of the test agent that inhibits cell growth by 50% at 24 hours of exposure. $IC_{50}$s were determined using the MTT assay or using the cell Titer-Glo method and following the instructions of the manufacturer (Invitrogen). As outlined in Sun, Y., and Rigas, B., (2008), traditional anti-cancer agents have $IC_{50}$s in these cell types on the order of 10 µM to 100 µM. (Sun, Y., and Rigas, B., (2008), Cancer Res., 68(20): 8269-8277). Accordingly, the $IC_{50}$s determined for anticancer peptides YJB01, YJB02, YJB03, and YJB04 establish their ability inhibit cancer cell growth in vitro. The $IC_{50}$s of control peptides YJB05 and YJB06 were determined to be greater than 2000 µM, evidencing a failure to effectively inhibit cancer cell growth in vitro.

TABLE 1

The $IC_{50}$s in HT29, SW480, BxPC3, MCF7, and MDA-MB-231 cell lines $IC_{50}$s, (µM)

| Cell line | YJB01 | YJB04 | YJB03 | YJB02 |
|---|---|---|---|---|
| SW480 | 34.7 | N/D | N/D | <12.5 |
| HT29 | 89 | 227 | 421 | N/D |
| BxPC3 | 109 | 123 | 153 | 36-76 |
| MCF7 | 68.9 | 25 | 21 | 213 |
| MDA-MB-231 | 88 | 195 | 309 | 243 |

(N/D: $IC_{50}$s for these peptides in these cell types were not determined).

Example 3

In vivo Xenograft Assay of Tumor Size

This example describes inhibition of colon cancer tumor growth in vivo by the anticancer peptide YJB01 in immunodeficient SCID mice.

Immunodeficient SCID mice (from Jackson Lab) were transplanted subcutaneously to their flank with 1.5 million SW480 human colon cancer cells. After the tumor size reached 120-150 mm$^3$, one mouse was treated with 100 µg YJB01 peptide injected intraperitoneally once a day, and the other one was treated with DMSO as a vehicle control. The tumor size was measured every two days (see FIG. 3A and FIG. 3B). The tumor volume was calculated based on its length (L) and width (W) using the formula Tumor volume=LW(L+W/2)0.56. (Rigas, B., and Kozoni, V., (2008) International Journal of Oncology, 32: 97-100). On the 10th day of treatment, the tumor volume was determined, the SCID mice were sacrificed and the tumors were excised and their weight was recorded (FIG. 3B).

After 10 days of treatment with the YJB01 peptide, there was almost no growth (−0.04% at day 10 comparing with day 1, as shown by the red line in FIG. 3A) of the tumor, whereas in the control animal (treated with vehicle only) the tumor size increased by 229%, as shown by the blue line in FIG. 3B.

Therefore, the anticancer peptide YJB01 inhibits colon cancer tumor growth in vivo.

Example 4

The Cytokinetic Effect of YJB01, YAMS and YJB06 Peptides on SW480 Human Colon Cancer Cells and MCF-7 Human Breast Cancer Cells SW480 human colon cancer cells and MCF7 breast cancer cells were grown following the instructions of American Type Culture Collection (ATCC, Monassas, Va.). The cells were treated with the test peptides for 24 hrs at concentrations ranging from 0 µM, to 200 µM and subjected to flow cytometry analysis following standard protocols. FIG. 4 shows the results of such analysis where, by determining the forward and side scatter, the proportion of dead cells is measured. The circumscribed (gated, outlined) areas in the figure indicate dead cells; dead cells generally have higher density (side scatter) and smaller size (forward scatter) than living cells.

Compared with YJB05 and YJB06, YJB01 had a greater cell killing effect in both cancer cell lines (studies with SW480 cells are show in FIG. 4A, studies with MCF7 cells are shown in FIG. 4B). Following treatment for 24 hr with 200 µM YJB01, 81.19% of SW480 and 72.12% of MCF7 cells were dead. However, following treatment for 24 hr with 200 µM YJB05 there were only 21.62% and 12.52% dead cells in SW480 and MCF7 cells, respectively. These findings indicate that the disulfide bond between the two cysteine residues is critical to the cell killing effect of these peptides. The cell killing effect of YJB06, which lacks the cell membrane permeable tail, was also tested in SW480 cells. As shown in FIG. 4A, YJB06 failed to kill SW480 colon cancer cells.

FIG. 5 shows the results of a similar analysis in which cells were stained with Annexin V to determine the proportion of apoptotic cells. When cells undergo apoptosis, the inner membrane phospholipid, phosphotidylserine (PS), flips to the outer membrane and can be recognized by the anti-Annexin V-FITC antibody. The green FITC fluorescence can be determined by flow cytometry and thus Annexin V (+) cells are apoptotic cells.

In this study, SW480 human cancer cells and MCF7 breast cancer cells were grown following the instructions of American Type Culture Collection (ATCC, Monassas, Va.). The cells were treated with the test peptides (YJB01, YJB05, or YJB06) for 24 hrs at concentrations ranging from 0 µM, to 200 µM. After treatment cells were trypsinized and stained with Annexin V-FITC (100× dilution) for 15 minutes. Annexin V-FITC fluorescence intensities were analyzed by FACSCaliber (BD Bioscience) following standard protocols. FIG. 5 demonstrates the cell killing effect of these peptides, confirming by an independent method the results shown in FIG. 4.

Example 5

Peptide YJB01 Induces Reactive Oxygen and Nitrogen Species

The levels of RONS in SW480 and MCF-7 cells were evaluated using the methodology described in Rigas, B., and Y. Sun. (2008), using the general RONS probe, dichlorodihydrofluorescein diacetate (DCFDA). (Rigas, B., and Sun., Y., (2008), *Br J Cancer* 98:1157-1160).

FIG. 6A shows the levels of RONS in SW480 cells treated with YJB01 at 20 µM and 100 µM (and negative control). SW480 human colon cancer cells were grown following the instructions of American Type Culture Collection (ATCC, Monassas, Va.). The cells were treated with the test peptide YJB01 for 1 hr at either 20 µM or 100 µM. After treatment, cells were trypsinized and stained with DCFDA (10 µmol/L) for 30 minutes at 37°. DCFDA fluorescence intensity was analyzed by FACSCaliber (BD Bioscience) following standard protocols. As illustrated in FIG. 5A, the Geometric Mean of the fluorescence intensity of DCFDA was increased significantly from 14.69 to 19.05 and then to 29.6 in SW480 cells after treatment with YJB01 (20 µM and 100 µM, respectively). Thus, FIG. 6A indicates YJB01 induces RONS production in a concentration dependent manner. This finding indicates that YJB01 induces RONS in SW480 colon cancer cells, creating a state of oxidative stress, and is responsible for its anticancer effect.

Example 6

Peptide YJB01 Induces the Oxidized Forms of Thioredoxin 1 and Peroxiredoxin 1

It has been demonstrated that several anti-cancer agents that act through a redox mechanism induce the oxidized form of thioredoxin 1. (Sun, Y., and Rigas, B. (2008), *Cancer Res.*, 68(20): 8269-8277). Therefore, the effect of YJB01 on thioredoxin 1 and peroxiredoxin was evaluated.

SW480 human colon cancer cells were grown following the instructions of American Type Culture Collection (ATCC, Monassas, Va.). Cells were treated with either no peptide, with YBJ01 (at 20 µM and 100 µM), or with YBJ05 (at 100 µM). $10^6$ cells from each sample were lysed in 6 mol/L guanidinium chloride, 50 mmol/L Tris/HCL (pH 8.3), 3 mmol/L EDTA, and 0.5% Triton-X-100 containing 50 mmol/L iodoacetic acid. After 30 min at 37° C., the excess idoacetic acid was removed using Microspin G-25 columns (GE Healthcare Life Sciences). Oxidized and reduced thioredxoin was separated by native PAGE. The gel was electroblotted onto a nitrocellulose membrane and probed with thioredoxin antibodies, followed by HRP-conjugated secondary antibody. Bands corresponding to thioredoxin were visualized by ECL.

The oxidized peroxiredoxin 1 (sulphonic-peroxiredoxin, Prx-O$_3$) was detected by using the specific anti-Prx-O3 antibody Briefly, after SW480 cells were treated with either no peptide, with YBJ01 (at 20 µM and 100 µM), or with YBJ05 (at 100 µM) for 1 h, total cell lysates were collected and separated on the SDS-PAGE gel. The gel was electroblotted onto a nitrocellulose membrane and probed with anti-Prx-O3, followed by HRP-conjugated secondary antibody. Bands corresponding to sulphonic-peroxiredoxin were visualized by ECL As shown in FIG. 6B, YJB01 induces the oxidized form of thioredoxin 1. This activity in contrast to YJB05, which failed to induce oxidation of thioredoxin 1. As noted above, YJB05 is ineffective in inhibiting the growth of the cells and inducing apoptosis.

The effect of these two peptides on the oxidized form of peroxiredoxin 1, an enzyme known to be involved in the redox regulation of the cell, was also evaluated. (Hall, A., et al., (2009) *Febs J*, 276:2469-2477; Aran, M., et al., (2009), *Febs J*, 276:2478-2493). As shown in FIG. 6B, peptide YJB01 induced the oxidized form of peroxiredoxin. This activity is in contrast to YJB05 which failed to induce oxidation. As noted above, YJB05 is ineffective in inhibiting the growth of the cells and inducing apoptosis.

Example 7

Peptide YJB01 Inhibits the Growth of SW480 Human Colon Cancer Xenografts in Nude Mice Xenografts were generated as described in the Example 3 except where noted. Each animal had two xenografts, one on its right flank and one on the left. In these studies, the effect of two doses of YJB01, 100 µg and 500 µg per animal were evaluated. The doses were administrated intraperitoneally once a day dissolved in phosphate buffered saline (PBS). Animals receiving the lower dose (3 controls and 4 treated with peptide YJB01) were treated for 21 days as shown in FIG. 7A. Those receiving the higher dose (8 controls and 8 treated with YJB01) were treated for 10 days as shown in FIG. 7B. Control animals were injected with PBS. Tumor volume was determined as described in Example 3. Tumor volume is expressed as mean±SEM. Administration of 100 μg YJB01 for 21 days significantly decreased tumor volume from 776 mm³ in the vehicle group to 527 mm³ (YJB01 group; p=0.016); this represents a 32% reduction in tumor volume. Administration of 500 μg YJB01 for 10 days significantly decreased tumor volume from 257 mm³ in the vehicle group to 102 mm³ (YJB01 group; p=0.016) representing a 60% reduction in tumor volume. It is worthy of emphasis that the higher dose of peptide YJB01 not only inhibited the growth of the tumor compared to control, but also decreased the tumor volume compared to its baseline; in other words, YJB01 caused tumor regression.

Example 8

Peptide YJB02 Inhibits the Growth of SW480 Human Colon Cancer Xenografts in Nude Mice This example describes inhibition of colon cancer tumor growth in vivo by the anticancer peptide YJB02 in nude mice bearing SW480 xenografts.

Xenografts were generated as described in the Example 3 except that 8 Balb/c nude mice in each group were used in this experiment. Nude mice bearing SW480 xenografts were treated with 500 μg/day of YJB02 for 19 days. The doses were administrated intraperitoneally once a day dissolved in phosphate buffered saline (PBS). Control animals were treated with PBS.

Tumor volume was determined as described in Example 3. Tumor volume was monitored and graphed as set forth in FIG. 9A, and is expressed as mean±SEM. The results indicate that administration of 500 μg/day of YJB02 for 19 days significantly decreased tumor volume from 635 mm³ in the control group to 207 mm³; this represents a 67% reduction in SW480 tumor growth.

Animals were euthanized at day 19 and the 4 representative mice bearing 2 control or 2 YJB02 treated tumors were photographed (see FIG. 9B). As shown in FIG. 9B, YJB02 inhibited SW480 tumor growth.

Example 9

The Anti-Cancer Effect of Peptide YJB02 Results from Induction of Apoptosis and Inhibition of Cell Proliferation This example describes the induction of apoptosis and inhibition of cell proliferation by peptide YJB02 in an in vitro study with SW480 tumor cells.

Tumor tissue from the mice treated with PBS or YJB02 as described in Example 8 were utilized in this experiment. Cell death was determined by terminal deoxynucleotidyl transferase dUTP nick end labeling (TUNEL) staining sections of paraffin embedded tissues, as previously described (Ouyang, N., Williams, J. L., Tsioulias, G. J., Gao, J., Iatropoulos, M. J., Kopelovich, L., Kashfi, K., and Rigas, B. 2006. Nitric oxide-donating aspirin prevents pancreatic cancer in a hamster tumor model. *Cancer Res* 66:4503-4511). Cell proliferation was determined by staining sections of paraffin embedded tissues for Ki-67 (Santa Cruz Biotechnology, Calif.) as previously described (Id.)

Slides were stained with TUNEL kit for apoptosis (available from Roche Applied Science, Indianapolis, Ind., US). As shown in the upper panel of FIG. 10, peptide YJB02 induced more TUNEL (+) cells than control tumors.

Tissue slides from control or YJB02 treated tumors were stained with anti-Ki67 antibody (Santa Cruz Biotechnology, Santa Cruz, Calif., US). As shown in the lower panel of FIG. 10, YJB02 inhibited tumor cell proliferation. The Ki67 (+) signals were dramatically decreased by YJB02. Slides were counter-stained with hematoxylin.

As shown by these results, the anti-cancer effect of YJB02 results from induction of apoptosis and inhibition of cell proliferation.

Example 10

Peptide YJB02 Specifically Targets Malignant Cells

This example describes the specific targeting of malignant cells by peptide YJB02 in an in vitro study.

The effect of peptide YJB02 on SW480 colon cancer cells was compared to the effect of peptide YJB02 on the normal human colon epithelial cell line NCM460. After 24-hour treatment with 200 μmol/L YJB02, only 20% SW480 cells remained viable. The viability was determined as described in Example 2. However, under the same experimental conditions, 75% of NCM460 cells were viable.

These results, set forth in FIG. 11, illustrate that peptide YJB02 specifically targets malignant cells.

Example 11

Peptide YJB02 Inhibits Thioredoxin Reductase Activity

This example illustrates inhibition of reductase activity by peptide YJB02 in an in vitro study.

Peptide YJB02 was incubated with thioredoxin reductase for 5 minutes and the reductase activity was measured following the instruction of the kit from Cayman chemical. This assay is based on the reduction of DTNB (5,5-dithio-bis(2-dinitrobenzoic acid) which produces a yellow product that is measured at 405-414 nm. The formula of the reaction is (TrxR+DTNB+NADPH+$H^+$→2TNB+$NADP^+$. The IC50 of YJB02 on thioredoxin reductase was 36 nM.

FIG. 12 shows an enzyme kinetic graph illustrating that peptide YJB02 inhibits thioredoxin reductase activity. The figure shows the standard thioredoxin reductase activity curve as a linear increase of the absorbance. The activity was determined based on the change in absorbance ($\Delta A412$) per minute ($\Delta A412$/min). As shown in FIG. 12, the $\Delta A412$/min decreased by YJB02 in a dose dependent manner.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated peptide or variant thereof, comprising an amino acid sequence that is at least 85% identical to the amino acid sequence set forth as SEQ ID NO:9, SEQ ID NO:10, SEQ ID NO:11, SEQ ID NO:12, SEQ ID NO:13, or SEQ ID NO:14.

2. The peptide or variant thereof according to claim 1 that is at least 85% identical to the amino acid sequence set forth as SEQ ID NO:11 and contains the sequence Cys-(y)N-Cys, wherein (y)N is Pro-Tyr.

3. The peptide or variant thereof according to claim 1 that is at least 85% identical to the amino acid sequence set forth as SEQ ID NO:10 and contains the sequence Cys-(y)N-Cys, wherein (y)N is Val-Asn-Val-Gly.

4. The peptide or variant thereof according to claim 1 that is at least 85% identical to the amino acid sequence set forth as SEQ ID NO:13 and contains the sequence Cys-(y)N-Cys, wherein (y)N is Gly-His.

5. The peptide or variant thereof according to claim 1 that is at least 85% identical to the amino acid sequence set forth as SEQ ID NO:14 and contains the sequence Cys-(y)N-Cys, wherein (y)N is Pro-His.

6. The peptide or variant thereof according to claim 1 that is at least 85% identical to the amino acid sequence set forth as SEQ ID NO:12 and contains the sequence Cys-(y)N-Cys, wherein (y)N is Pro-Val.

7. The peptide or variant thereof according to claim 1 that is at least 85% identical to the amino acid sequence set forth as SEQ ID NO:9 and contains the sequence Cys-(y)N-Cys, wherein (y)N is Gly-Pro.

8. The isolated peptide of claim 1, wherein the peptide comprises the amino acid sequence set forth as SEQ ID NO:9.

9. The isolated peptide of claim 1, wherein the peptide consists of the amino acid sequence set forth as SEQ ID NO:9.

10. The isolated peptide of claim 1, wherein the peptide comprises the amino acid sequence set forth as SEQ ID NO:10.

11. The isolated peptide of claim 1, wherein the peptide consists of the amino acid sequence set forth as SEQ ID NO:10.

12. The isolated peptide of claim 1, wherein the peptide comprises the amino acid sequence set forth as SEQ ID NO:11.

13. The isolated peptide of claim 1, wherein the peptide consists of the amino acid sequence set forth as SEQ ID NO:11.

14. The isolated peptide of claim 1, wherein the peptide comprises the amino acid sequence set forth as SEQ ID NO:12.

15. The isolated peptide of claim 1, wherein the peptide consists of the amino acid sequence set forth as SEQ ID NO:12.

16. The isolated peptide of claim 1, wherein the peptide comprises the amino acid sequence set forth as SEQ ID NO:13.

17. The isolated peptide of claim 1, wherein the peptide consists of the amino acid sequence set forth as SEQ ID NO:13.

18. The isolated peptide of claim 1, wherein the peptide comprises the amino acid sequence set forth as SEQ ID NO:14.

19. The isolated peptide of claim 1, wherein the peptide consists of the amino acid sequence set forth as SEQ ID NO:14.

20. A pharmaceutical composition comprising a peptide or variant thereof according to any one of claims 1-7 and 16-19 and a pharmaceutically acceptable carrier.

21. The pharmaceutical composition of claim 20, wherein the pharmaceutically accepted carrier is selected from the group consisting of: a cell penetrating peptide, a liposome, and a dendrimer.

22. The pharmaceutical composition of claim 21, wherein the carrier is a liposome.

23. The pharmaceutical composition of claim 22 wherein the liposome comprises a targeting agent.

24. The pharmaceutical composition of claim 23, wherein the targeting agent is selected from the group consisting of antibodies and antibody mimetics.

25. A method of treating colon cancer in a subject comprising administering to the subject a therapeutically effective amount of a peptide or variant thereof, comprising an amino acid sequence that is at least 85% identical to the amino acid sequence set forth as SEQ ID NO:9, SEQ ID NO:10, SEQ ID NO:11, SEQ ID NO:12, SEQ ID NO:13, or SEQ ID NO:14, and contains the sequence Cys-(y)N-Cys, wherein (y)N is Gly-Pro, Val-Asn-Val-Gly, Phe-Tyr, Pro-Val, Gly-His, or Pro-His, respectively.

26. The method of claim 25, wherein the peptide or variant thereof is at least 85% identical to the amino acid sequence set forth as SEQ ID NO:9 and contains the sequence Cys-(y)N-Cys, wherein (y)N is Gly-Pro.

27. The method of claim 25, wherein the peptide or variant thereof is at least 85% identical to the amino acid sequence set forth as SEQ ID NO:11 and contains the sequence Cys-(y)N-Cys, wherein (y)N is Pro-Tyr.

28. The method of claim 25, wherein the peptide or variant thereof is at least 85% identical to the amino acid sequence set forth as SEQ ID NO:10 and contains the sequence Cys-(y)N-Cys, wherein (y)N is Val-Asn-Val-Gly.

29. The method of claim 25, wherein the peptide or variant thereof is at least 85% identical to the amino acid sequence set forth as SEQ ID NO:13 and contains the sequence Cys-(y)N-Cys, wherein (y)N is Gly-His.

30. The method of claim 25, wherein the peptide or variant thereof is at least 85% identical to the amino acid sequence set forth as SEQ ID NO:14 and contains the sequence Cys-(y)N-Cys, wherein (y)N is Pro-His.

31. The method of claim 25, wherein the peptide or variant thereof is at least 85% identical to the amino acid sequence set forth as SEQ ID NO:12 and contains the sequence Cys-(y)N-Cys, wherein (y)N is Pro-Val.

32. The method of claim 25, further comprising administering to the subject one or more additional anti-cancer agents.

33. The method of claim 32 wherein the peptide and one or more additional anti-cancer agents are incorporated into a liposome.

34. The method of claim 33, wherein the anti-cancer agent(s) is a chemotherapeutic agent.

35. The method of claim 25, wherein the cancer is inhibited by induction of apoptosis.

36. The method of claim 25, wherein the cancer is inhibited by inhibition of cell proliferation.

37. The method according to claim 25, wherein the subject is human.

38. The method of claim 25, wherein the peptide or variant thereof comprises the amino acid sequence set forth as SEQ ID NO:9, SEQ ID NO:10, SEQ ID NO:11, SEQ ID NO:12, SEQ ID NO:13, or SEQ ID NO:14.

39. The method of claim 25, wherein the peptide or variant thereof consists of the amino acid sequence set forth as SEQ ID NO:9, SEQ ID NO:10, SEQ ID NO:11, SEQ ID NO:12, SEQ ID NO:13, or SEQ ID NO:14.

* * * * *